United States Patent [19]
Strobel et al.

[11] Patent Number: 5,766,473
[45] Date of Patent: Jun. 16, 1998

[54] ENZYME LOADED HYDROPHILIC POROUS STRUCTURE FOR PROTECTING OXYGEN SENSITIVE PRODUCTS AND METHOD FOR PREPARING SAME

[75] Inventors: Joan M. Strobel, Maplewood; David R. Gagnon, St. Paul, both of Minn.

[73] Assignee: Minnesota Mining and Manufacturing Company, Saint Paul, Minn.

[21] Appl. No.: 456,888

[22] Filed: Jun. 1, 1995

Related U.S. Application Data

[62] Division of Ser. No. 122,807, Sep. 16, 1993, Pat. No. 5,443,727, which is a continuation of Ser. No. 775,969, Nov. 8, 1991, abandoned, which is a continuation-in-part of Ser. No. 605,834, Oct. 30, 1990, abandoned, and a continuation-in-part of Ser. No. 605,754, Oct. 30, 1990, abandoned, and a continuation-in-part of Ser. No. 605,948, Oct. 30, 1990, abandoned, and a continuation-in-part of Ser. No. 605,921, Oct. 30, 1990, abandoned, and a continuation-in-part of Ser. No. 605,828, Oct. 30, 1990, abandoned, and a continuation-in-part of Ser. No. 605,757, Oct. 30, 1990, abandoned.

[51] Int. Cl.$^6$ ............................................. B01D 71/38
[52] U.S. Cl. .................... 210/490; 210/500.42; 428/35.4
[58] Field of Search ........................... 210/500.42, 490; 428/308.4, 35.4, 35.7; 426/124, 127

[56] References Cited

U.S. PATENT DOCUMENTS

| | | | |
|---|---|---|---|
| 2,765,233 | 10/1956 | Sarett et al. | 99/178 |
| 3,853,601 | 12/1974 | Taskier | 117/98 |
| 3,892,575 | 7/1975 | Watts et al. | 96/84 R |
| 3,941,718 | 3/1976 | Barabas et al. | 252/430 |
| 4,143,218 | 3/1979 | Adams et al. | 429/254 |
| 4,192,773 | 3/1980 | Yoshikawa et al. | 525/429 |
| 4,197,181 | 4/1980 | Portal et al. | 204/283 |
| 4,298,666 | 11/1981 | Taskier | 429/206 |

(List continued on next page.)

FOREIGN PATENT DOCUMENTS

| | | |
|---|---|---|
| 0 203 459 | 5/1986 | European Pat. Off. |
| 0 272 923 | 6/1988 | European Pat. Off. |
| 0 359 925 | 7/1989 | European Pat. Off. |
| 0 370 657 | 11/1989 | European Pat. Off. |
| 28 17 854 | 1/1979 | Germany |
| 50-139184 | 6/1975 | Japan |
| 62-14903 | 1/1987 | Japan |
| 62-277106 | 12/1987 | Japan |
| 1 601 529 | 10/1981 | United Kingdom |

OTHER PUBLICATIONS

Harris, *J. Polymer Sci.*, Part A–1, vol. 4, 665–677 (1965).
Haas et al., *J. Polymer Sci.*, vol. 22, 291–302 (1956).
Ikada et al., "Blood Compatibility of Hydrophilic Polymers, ", *J. Biomedical Materials Research*, 15:697–718, (1981).
Sato et al., "Study on Interactions Between Plasma Proteins and Ploymer Surface", *Polymer Journal*, 16: No. 1, pp. 1–8 (1984).

(List continued on next page.)

*Primary Examiner*—Frank Spear
*Attorney, Agent, or Firm*—Gary L. Griswold; Walter N. Kirn; John H. Hornickel

[57] ABSTRACT

Articles having a complex geometric configuration have hydrophilicity imparted to at least a portion of surfaces of the articles while substantially retaining the complex geometric configuration. The hydrophilicity is imparted by an extremely thin, self-interlocking shell of tactic, hydrophilic poly(vinyl alcohol) enveloping the surfaces. A tactic poly(vinyl alcohol) precursor applied to surfaces of the supporting structure is reacted in situ on the surfaces with a hydrolysis reagent to prepare the tactic, hydrophilic poly(vinyl alcohol) shell. The article having the hydrophilic shell is highly resistant to solvent washout. Hydrophilicity and hydrophobicity can be reversibly provided on regio-specific surfaces of the article. Hydrophilic porous supporting structures loaded with an enzyme system which catalyzes a reaction of a substrate, oxygen, and if necessary, water or moisture to consume oxygen are also described for oxygen scavenging in packages containing oxygen sensitive products.

14 Claims, 3 Drawing Sheets

U.S. PATENT DOCUMENTS

| | | | |
|---|---|---|---|
| 4,301,195 | 11/1981 | Mercer et al. | 427/261 |
| 4,302,334 | 11/1981 | Jakabhazy et al. | 210/500.2 |
| 4,328,076 | 5/1982 | Fisher et al. | 204/14 R |
| 4,342,635 | 8/1982 | Becker et al. | 204/263 |
| 4,346,142 | 8/1982 | Lazear | 428/315.7 |
| 4,354,308 | 10/1982 | Shimada et al. | 29/571 |
| 4,394,457 | 7/1983 | Ogasa | 521/54 |
| 4,438,185 | 3/1984 | Taskier | 429/250 |
| 4,440,830 | 4/1984 | Wempe | 428/352 |
| 4,501,793 | 2/1985 | Sarada | 428/315.5 |
| 4,524,015 | 6/1985 | Takahashi et al. | 252/188.28 |
| 4,528,325 | 7/1985 | Ofstead | 252/60 |
| 4,615,784 | 10/1986 | Stewart et al. | 204/263 |
| 4,618,649 | 10/1986 | Ofstead | 525/60 |
| 4,640,865 | 2/1987 | Lancaster et al. | 428/421 |
| 4,675,213 | 6/1987 | Yamamori et al. | 427/244 |
| 4,687,481 | 8/1987 | Nuwayser | 604/897 |
| 4,693,939 | 9/1987 | Ofstead | 428/421 |
| 4,694,037 | 9/1987 | Ofstead | 524/557 |
| 4,749,487 | 6/1988 | Lefebvre | 210/490 |
| 4,753,725 | 6/1988 | Linder et al. | 210/654 |
| 4,776,959 | 10/1988 | Kasai et al. | 210/490 |
| 4,778,596 | 10/1988 | Linder et al. | 210/638 |
| 4,780,514 | 10/1988 | Ofstead | 526/245 |
| 4,794,002 | 12/1988 | Henis et al. | 424/488 |
| 4,840,992 | 6/1989 | Ofstead | 525/61 |
| 4,849,224 | 7/1989 | Chang et al. | 424/434 |
| 4,849,457 | 7/1989 | Ichii et al. | 521/62 |
| 4,861,644 | 8/1989 | Young et al. | 428/195 |
| 4,878,212 | 10/1989 | Kuder | 369/100 |
| 4,885,086 | 12/1989 | Miura | 210/321.8 |
| 4,894,253 | 1/1990 | Heineman et al. | 427/36 |
| 4,911,844 | 3/1990 | Linder et al. | 210/638 |
| 4,917,895 | 4/1990 | Lee et al. | 424/448 |
| 4,921,884 | 5/1990 | Hammer et al. | 523/106 |
| 4,921,908 | 5/1990 | Ofstead | 525/61 |
| 4,943,373 | 7/1990 | Onishi et al. | 210/500.42 |
| 4,943,374 | 7/1990 | Heininger et al. | 210/651 |
| 4,944,879 | 7/1990 | Steuck | 210/500.27 |
| 4,963,494 | 10/1990 | Hibino et al. | 435/288 |
| 5,006,216 | 4/1991 | Dietrich et al. | 204/257 |
| 5,037,656 | 8/1991 | Pitt et al. | 424/443 |
| 5,041,225 | 8/1991 | Norman | 210/500.36 |
| 5,049,275 | 9/1991 | Gillberg-LaForce et al. | 210/500.27 |
| 5,064,698 | 11/1991 | Courtright et al. | 428/35.4 |
| 5,091,299 | 2/1992 | Turner et al. | 435/4 |
| 5,443,727 | 8/1995 | Gagnon | 210/490 |

OTHER PUBLICATIONS

Saito, "On Food Quality Preservation By Means of Free Oxygen Absorber", *Journal Yukaqaku*, 28, No. 1, pp. 45–54 (1979) (Translated with pagination 1–23).

Labuza et al., "Applications of Active Packaging for Improvement of Shelf Life and Nutritional Quality of CAP/MAP Foods", *J. Food Processing and Preservation*, 13:1–69 (1989).

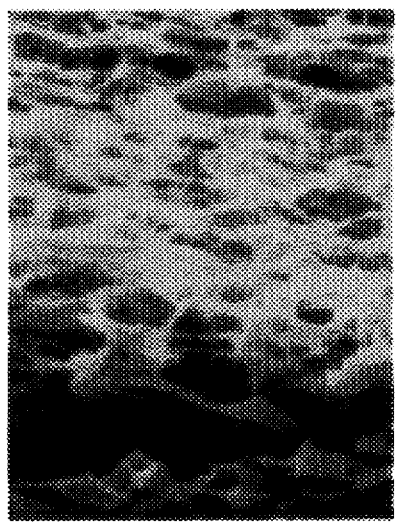 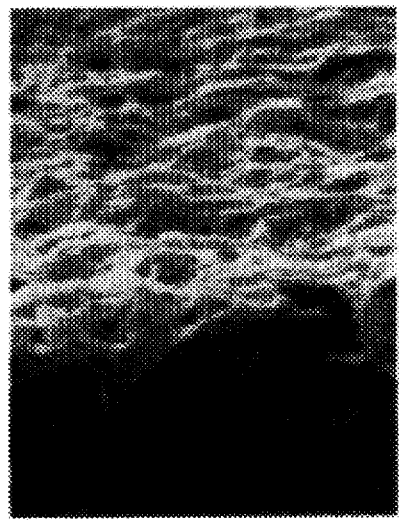
1μm
Fig. 2a
1μm
Fig. 2b

ENZYME LOADED HYDROPHILIC POROUS STRUCTURE FOR PROTECTING OXYGEN SENSITIVE PRODUCTS AND METHOD FOR PREPARING SAME

RELATED APPLICATIONS

This application is a division of U.S. patent application Ser. No. 08/122,807 filed Sep. 16, 1993, now U.S. Pat. No. 5,443,127 which is a continuation of U.S. patent application Ser. No. 07/775,969 filed Nov. 8, 1991, abandoned, which is a continuation-in-part of U.S. patent application Ser. No. 07/605,834 filed Oct. 30, 1990, abandoned, and a continuation-in-part of U.S. patent application Ser. No. 07/605,754 filed Oct. 30, 1990, abandoned, and a continuation-in-part of U.S. patent application Ser. No. 07/605,948 filed Oct. 30, 1990, abandoned, and a continuation-in-part of Ser. No. 07/605,921 filed Oct. 30, 1990, abandoned, and a continuation-in-part of Ser. No. 07/605,828 filed Oct. 30, 1990, abandoned, and a continuation-in-part of Ser. No. 07/605,757 filed Oct. 30, 1990, abandoned. All prior related applications are incorporated by reference herein.

FIELD OF THE INVENTION

This invention relates to a porous structure having an extremely thin hydrophilic polymeric shell over a complex geometric configuration of the structure which is loaded with an oxidase enzyme, the use of such enzymatically active material to protect oxygen sensitive products, and the method of preparing such material.

BACKGROUND OF THE INVENTION

Many polymeric materials are hydrophobic. When such materials are formed into films, beads, membranes or the like, their hydrophobic nature prevents or inhibits "wetting" by water.

When used to describe a surface, the term "hydrophobic" means that water on that surface has a contact angle of greater than ninety degrees. By contrast, the term "hydrophilic" applies to those polymeric surfaces which have a contact angle of less than ninety degrees.

While hydrophobic materials are well known in the art and easily prepared, their usefulness in many processes and products is severely restricted by their hydrophobicity. There have been numerous prior attempts to render a hydrophobic material hydrophilic in order to be useful in processes where water is present and must "wet" the surface of the material.

Several efforts have concentrated in rendering hydrophilic a porous hydrophobic polymeric membrane. Despite the low cost of preparation of such hydrophobic materials in the form of porous membranes, such membranes are not useful as membranes in aqueous systems because capillary forces at the pores of such hydrophobic materials prevent the wetting of the pores by water, aqueous solutions, or other high surface tension organic solutions.

Treatment of the surfaces of hydrophobic materials, such as porous membranes, made from polyolefins has been attempted using surfactant coatings such as the silicone glycol copolymer disclosed in U.S. Pat. No. 3,853,601 (Taskier) or the nonionic alkylphenoxy poly(ethyleneoxy) ethanol surfactant disclosed in U.S. Pat. No. 4,501,793 (Sarada), or a copolymer coating having hydrophilic monomeric units and hydrophobic monomeric units such as an ethylene-vinyl alcohol copolymer disclosed in European Patent Office Publication No. 0 023 459 (Nitadori et al.).

Unfortunately, such surfactant treatments to the surfaces of hydrophobic materials may not be permanent due to the washing away of such surface coatings by water or a variety of organic solvents including those used to form the coating on the supporting hydrophobic article. Also, surfactants are commonly known to denature enzymes. See, for example, Molecular Cell Biology, J. Darnell et al. Fds., Scientific American Books, 232, (1986).

Another approach taken in the art is the adsorption of a hydrophilic polymer on a hydrophobic substrate, as disclosed in U.S. Pat. No. 4,794,002 and corresponding European Patent Office Publication 0 221 046 (Henis et al.). A modifying polymer may be adsorbed onto the surfaces of a polysulfone or a polyethersulfone from an aqueous solution of the modifying polymer. But the modifying polymer can be removed with detergent solutions and the like.

Relatively permanent hydrophilic coatings on hydrophobic microporous films have been attempted by further treatment of chemical cross-linking of or ionizing radiation directed against the coating. U.S. Pat. No. 4,346,142 (Lazear) discloses an ionizing radiation process. U.S. Pat. No. 4,776,959 (Kasai et al.) discloses thermally curing a water insoluble vinyl alcohol-vinyl acetate copolymer onto a porous membrane. U.S. Pat. No. 4,753,725 (Linder et al.) discloses semipermeable composite membranes made by reacting PVA/PVA-copolymer films with a monomeric organic compound containing at least two functional groups, a linear or branched polyfunctional oligomer or polymer, and a compound containing cross-linking and ionizable groups. Japanese Publ. No. JP62-14903 (Ohtani et al.) describes using a solution containing a compound having ester side chains and a crosslinking agent to thermally crosslink the ester side chains to hydroxyl or carboxyl reactive sites on the hydrophobic polymer.

Others have attempted to apply hydrophilic poly(vinyl alcohol) directly to the hydrophobic polymer membrane. Japanese Publ. No. JP62-277106 (Ikehara et al.) describes the ionic cross-linking of a poly(vinyl alcohol) on a microporous polymer substrate from a water-soluble poly (vinyl alcohol) polymer containing an inorganic alkaline compound. While poly(vinyl alcohol) has excellent hydrophilicity, processing difficulties are encountered when one attempts to coat hydrophilic poly(vinyl alcohol) directly onto the hydrophobic membrane from a polar or aqueous solution.

Another has attempted to form hollow fiber microporous membranes with poly(vinyl alcohol) chemically bonded to the surfaces of the hollow fiber membrane. U.S. Pat. No. 4,885,086 (Miura) discloses that a hollow fiber membrane is irradiated with ionizing radiations and then reacted with vinyl acetate and hydrolyzed.

The attempts described in the art to provide a hydrophilic poly(vinyl alcohol) coating are based on using atactic poly (vinyl alcohol), which has a low crystallinity content. It is believed that coatings based on atactic poly(vinyl alcohol) are more soluble in a range of solvents and aqueous fluids and consequently the coatings are more readily washed away, particularly when contacted with solvents miscible with the solvents used to bring the hydrophilic material in contact with the hydrophobic membrane.

It is possible to produce poly(vinyl alcohol) which is not atactic. Preparation and the properties of syndiotactic and isotactic poly(vinyl alcohol) have been described in Harris et al., Journal of Polymer Science: Part A-1, Vol. 4, 665–677 (1966), describing the preparation of syndiotactic poly(vinyl alcohol) from poly(vinyl trifluoroacetate) and isotactic poly (vinyl alcohol) from poly(vinyl tert-butyl ether). Further, the production of poly(vinyl trifluoroacetate) as a precursor for syndiotactic poly(vinyl alcohol) has been described in Haas et al., Journal of Polymer Science, Vol. 22, pgs. 291–302 (1956).

Prior uses of such tactic poly(vinyl alcohol) materials have included the preparation of ophthalmic articles, such as contact lenses and coatings for such articles, from non-crosslinked poly(vinyl alcohol) copolymers hydrated to have controlled hydrogel properties and high strength. Co-assigned, related U.S. Pat. Nos. 4,528,325; 4,618,649; 4,693,939; 4,694,037; 4,780,514; 4,840,992; and 4,921,908 (Ofstead) disclose these copolymers and shaped articles, with U.S. Pat. No. 4,693,939 disclosing these copolymers as coatings on articles.

Non-crosslinked crystallized poly(vinyl alcohol) coatings have been disclosed for use with a variety of medical devices. European Patent Publication 0 370 657 (Ofstead) discloses a poly(vinyl alcohol) coating on medical devices (such as catheter guidewires), which is prepared by coating atactic poly(vinyl alcohol) on the device and then annealing the coating to crystallize the poly(vinyl alcohol) to provide a slippery surface.

However, the art of preparing crystallized poly(vinyl alcohol) hydrogel coatings has failed to recognize that in many instances it is desirable to retain the particular geometric configuration of the article being coated. Crystallized poly(vinyl alcohol) which is capable of becoming a hydrogel in the presence of water can disrupt a complex geometric configuration of a supporting structure, such as by blocking the pores of a microporous membrane, if the coating applied to the supporting structure is not carefully controlled.

Oxygen Scavengers

Certain food products are subject to deterioration upon exposure to atmospheric oxygen during storage. Previous methods of preserving such materials have included: freezer storage, (which is not practical for many foodstuffs); vacuum packaging, (which is not practical for fragile foods); gas-flushing the package with an inert gas prior to sealing the package (which is largely ineffective due to package oxygen permeability); and more recently, the use of oxygen-reactive materials as scavengers. A survey of oxygen scavengers such as inorganic dithionite salts, specially processed iron powders, and sugar-based alkali denatured products used to preserve the quality of food is described in Saito, "On Food Quality Preservation By Means of Free Oxygen Absorber," Journal Yukagaku, 28, No. 1 (1979), pp 1–23. Oxygen scavenging systems are also described in Labuza et al., "Applications of Active Packaging for Improvement of Shelf Life and Nutritional Quality of CAP/MAP Foods", J. Food Processing and Preservation, 13: 1–69; 1989.

The specially processed iron powders are often packaged in gas-permeable pouches and added to he package containing the food product. See, for example, the disclosures of U.S. Pat. Nos. 4,192,773 (Yoshikawa et al.) and 4,524,015 (Takahashi et al.). But these sachets added to food packaging complicate the food processing automated operations and are not generally favored by consumers.

An enzyme treated fabric sheet for wrapping a moist food product is disclosed in U.S. Pat. No. 2,765,233 (Sarett et al.). The enzyme system on the surface of the sheet will be in contact with the article being wrapped and is preferably in a water dispersible binder. If the article does not contain glucose, the sheet may be coated or impregnated with glucose along with the enzyme system. The system relies on a two step oxidation reaction of glucose, glucose oxidase, oxygen, and water found at the interface between the moist food product and the outer surface of the wrapping sheet.

Likewise, Japanese patent publication JP 75/139184 (Okada et al.) describes a food packaging film thickly coated with enzymes and glucose in a water soluble binder.

SUMMARY OF THE INVENTION

The present invention describes a supporting structure having a complex geometric configuration and an extremely thin hydrophilic polymer shell which imparts hydrophilicity to the structure. The present invention also describes a method of providing such hydrophilicity while substantially retaining the geometric configuration of the structure.

The invention overcomes the deficiencies in the prior art by providing a supporting structure having a complex geometric configuration enveloped at at least a portion of its surfaces by an extremely thin, self-interlocking shell of tactic, hydrophilic homopolymer or copolymer of poly(vinyl alcohol) while substantially retaining the complex geometric configuration of the supporting structure. The tactic poly (vinyl alcohol) shell may be either syndiotactic or isotactic.

As used herein, "complex geometric configuration" refers to the multiplicity and types of surfaces of a supporting structure when observed on a micron scale. The extremely thin shell of poly(vinyl alcohol) on a supporting structure envelops the multiplicity of such surfaces without altering the type of such surfaces. Thus, the poly(vinyl alcohol) shell imparts hydrophilicity to a supporting structure while substantially retaining the complex geometric configuration of the supporting structure.

The multiplicity of surfaces of a supporting structure are enveloped by the poly(vinyl alcohol) shell. "Envelop" means the shell entirely surrounds each of the multiple surfaces and imparts hydrophilicity thereto. Integrity is imparted by the formation of crystalline crosslinks within the shell, i.e., the formation of tie molecules connecting two or more crystallites. Thus, the shell is self-interlocking mechanically about the surfaces of the supporting structure without substantial covalent, ionic, or van der Waals interaction with such surfaces.

The type of surfaces that a supporting structure may have may be expressed in terms of Euclidean geometry, fractal geometry, or a combination of both.

A fractal is an object or process that cannot be represented by Euclidean geometry. With the complexity of natural shapes and surfaces being so jagged that they have more than two dimensions, fractal geometry has become useful to analyze shapes so commonly found in nature. (Van Nostrand's Scientific Encyclopedia Seventh Edition, Van Nostrand Reinhold 1989, p. 1221.)

Euclidean surfaces may be planar, curved, or any other topography which may exhibit a Euclidean geometric configuration.

Fractal surfaces may be porous, tentacular, jagged, uneven, undulating, irregular, asymmetrical, or of any other topography which may exhibit a non-Euclidean geometric configuration.

For example, a porous membrane or bead may appear to have surfaces which are planar or spherical, respectively, i.e., in a Euclidean geometric configuration. But at a micron scale, the membrane and bead have a complex geometric configuration, because a precise examination of the multiplicity of surfaces shows a fractal, three dimensional terrain which defies Euclidean characterization. The pores of the membrane or bead are uneven, irregular, and unpatterned in all of the three dimensions Euclidean geometry measures. The fractal surfaces surrounding such pores generate a complex geometric configuration for the supporting fractal structure. The poly(vinyl alcohol) shell of the present invention envelops such fractal surfaces defining such pores but does not cover or fill such pores or otherwise convert the fractal configuration of the surfaces to a Euclidean configuration.

In another example, a non-woven web may appear to be flat and have a Euclidean geometric configuration. But at a micron scale, surfaces of the web are an unpatterned layering of strands which give the non-woven web a complex geometric configuration, even if the individual strands comprising the web have a Euclidean geometric configuration. The poly(vinyl alcohol) shell of the present invention envelops the strands of the web while substantially retaining the complexity of the surfaces and the fractal configuration of the non woven web.

The hydrophilic, polymeric shell enveloping the supporting structure is "extremely thin", on a scale of monolayers of polymer. "Extremely thin" means that the shell's monolayer dimension is such that it does not substantially clog, smooth, block, or swell in manner to appreciably alter a supporting structure's complex geometry. Unlike a hydrogel coating, which, upon exposure to water would swell and significantly alter a geometric configuration of a supporting structure, the self-interlocking shell of poly(vinyl alcohol) of the articles of the present invention does not appreciably swell, substantially retaining the complex geometry of the article.

A supporting structure such as a membrane may have a Bubble Point Pore Size (c.f ASTM F-316) of about 0.01 to 20 μm. The present invention finds that an extremely thin shell of hydrophilic polymer having less than about an average of 100 Angstroms thickness forming a shell on fractal surfaces of the membrane reduces the effective pore size less than about 30 percent and desirably less than about 15 percent. The complex geometric configuration of the supporting structure is substantially retained.

Thus, the present invention allows the supporting structure to acquire a hydrophilic surface without altering its physical configuration.

The supporting structure has at least one surface in a complex geometric configuration which the poly(vinyl alcohol) shell may envelop. Nonlimiting examples of a supporting structure include films, porous membranes, beads, woven and non-woven webs, spun threads, hollow porous fibers, and porous fibers. Nonlimiting examples of the composition of the supporting structure may be polymeric, ceramic, cellulosic, glassy, metallic, or carbonaceous.

A polymeric structure may be made from any useful and formable polymeric material which does not dissolve substantially in the presence of solvents used with precursors to make the shell. Nonlimiting examples include without limitation, polyolefins (e.g., polyethylene and polypropylene), polyhalo olefins (e.g., polytetrafluoroethylene and polyvinylidene fluoride), nylon, polyesters (e.g., polyethylene terephthalate), polysulfones, polyethersulfones, poly(2,6-dimethyl,4-phenylene oxide) and derivatives thereof, polyamides, polyimides, polyetherimides, or polymeric materials previously unavailable for forming hydrophilic polymeric structures.

The tactic, hydrophilic shell of a homopolymer or copolymer of poly(vinyl alcohol) is formed in-situ about complex, envelopable surfaces of the supporting structure by hydrolysis (e.g., alcoholysis or ammonolysis) of a tactic hydrophobic polymeric poly(vinyl alcohol) precursor with a hydrolysis reagent.

"Hydrolysis" means the cleaving of an ester or ether group in the presence of a hydrolysis reagent to form an alcohol group.

The hydrophobic polymeric poly(vinyl alcohol) precursor can be any tactic poly(vinyl alcohol) precursor which forms a tactic homopolymer or copolymer of poly(vinyl alcohol), including without limitation, homopolymers of vinyltrifluoroacetate and copolymers of vinyltrifluoroacetate monomers and monomers having a vinylic group therein, homopolymers of vinyl tert-butyl ether monomers, and copolymers of vinyl tert-butyl ether monomers and monomers having a vinylic group therein. For purposes of describing this invention, references to poly(vinyl alcohol) shall include both a homopolymer of poly(vinyl alcohol) and a copolymer of vinyl alcohol and another co-monomer.

The invention also overcomes problems confronted in the prior art by providing a method for generating an extremely thin shell of tactic poly(vinyl alcohol) about envelopable surface(s) of a supporting structure. The method employs applying a tactic, polymeric poly(vinyl alcohol) precursor to surfaces of the supporting structure, and then causing, in-situ, a hydrolysis reaction to form a tactic, hydrophilic poly(vinyl alcohol) shell enveloping such surfaces while retaining the complex geometric configuration of the supporting structure.

The hydrolysis reagent may be a reagent which causes the formation of tactic poly(vinyl alcohol), whether such reaction occurs in liquid or gaseous phase. Preferably, the hydrolysis reagent is a basic reagent having a pH greater than about 7.0. Suitable reagents include, but are not limited to, dissolved or anhydrous ammonia, sodium hydroxide, sodium carbonate, and potassium hydroxide.

Many desirable articles having a hydrophilic polymeric shell thereon may be made and used in accordance with the present invention. The article may take the form of porous membranes where fractal surfaces define pores and interstices in and through the membrane. The shell of poly(vinyl alcohol) does not substantially alter the complex geometric configuration of the membrane. Such membranes may be used to separate particles in a flowing medium.

The present invention provides a hydrophilic polymeric self-interlocking shell about surfaces of a supporting structure while substantially retaining the complex geometric configuration of the structure, and to permit that hydrophilized article to be used in aqueous systems or with organic solvents without adversely affecting the hydrophilic polymeric shell.

The present invention also provides a method for forming an extremely thin shell of tactic, hydrophilic poly(vinyl alcohol) about a supporting structure, such as a microporous membrane, through the use of a tactic poly(vinyl alcohol) precursor capable of being converted, in-situ, on at least a portion of the complex surfaces of the supporting structure to tactic poly(vinyl alcohol) while substantially retaining the complex geometric configuration of the structure.

A feature of the invention is that the hydrophilic polymeric shell may be prepared using readily available materials reacted at minimally elevated temperatures and pressures.

It is another feature of the invention that the extremely thin hydrophilic polymeric shell of tactic hydrophilic poly(vinyl alcohol) envelops all outer surfaces of the supporting structure and any available interior surfaces without blocking or clogging such pores or interstices or otherwise substantially altering the complex geometric configuration of the supporting structure.

It is another feature of the invention to provide a tactic hydrophilic poly(vinyl alcohol) shell on a supporting structure which has hydroxyl reactive sites available for further reaction.

It is an advantage of the invention that articles produced according to the present invention have a surface shell which is permanent in the presence of aqueous systems or organic solvents, including those employed during use of a hydrophilic article.

It is another advantage of the invention that the tactic, hydrophilic poly(vinyl alcohol) shell provides increased mechanical strength to the polymeric structure, thereby enhancing the stability and sturdiness of an otherwise delicate film, membrane, web, or other structure while substantially retaining the physical configuration of that structure.

The present invention also provides an oxygen scavenger to protect oxygen sensitive products. The oxygen scavenger comprises a hydrophilic porous supporting structure having a complex geometric configuration of porous surfaces and an enzyme system loaded on said surfaces to catalyze at said surfaces the reaction of a substrate, oxygen and, if necessary, water or moisture, to consume the oxygen.

The present invention also provides an oxygen scavenging package to protect an oxygen sensitive product. The package comprises a container capable of being sealed to minimize intrusion of molecular oxygen into the container and the oxygen scavenger.

"Enzyme system" means an enzyme or a mixture of an enzyme and a substrate or other compounds. The enzyme system catalyzes a reaction between oxygen, a substrate, and if necessary, water or moisture, to form a converted substrate. Most often, a sugar is the substrate which is converted by reaction with oxygen and water to form a sugar acid. The enzyme catalyzed reaction consumes oxygen and continues to scavenge oxygen from the reaction environment.

The present invention also overcomes the deficiencies in the prior art by providing a hydrophilic porous supporting structure having a complex geometric configuration into which an enzyme system may be loaded without the need for a water-dispersible binder.

Preferably, the hydrophilic porous structure may be a porous structure which is enveloped by an extremely thin self-interlocking shell of tactic, hydrophilic homopolymer or copolymer of poly(vinyl alcohol) while substantially retaining the complex geometric configuration of the porous supporting structure. Because hydrophilic surfaces are wet by the water-miscible solvent used to load the enzyme system, the hydrophilic porous supporting structure may then be loaded with an enzyme system, to react with oxygen present within a package containing an oxygen sensitive product. The tactic poly(vinyl alcohol) shell may be either syndiotactic or isotactic.

Thus, the present invention allows the hydrophilic porous supporting structure to be loaded with an enzyme system within the complex geometric configuration of the porous structure in order to catalyze an oxygen scavenging reaction.

The invention also overcomes problems confronted in the prior art by providing a method for loading of an enzyme system on hydrophilic surfaces without denaturing the enzymatically active material. The method employs applying a tactic, polymeric poly(vinyl alcohol) precursor on surfaces of the porous supporting structure, and then causing, in-situ, a hydrolysis with a hydrolysis reagent to form a tactic, hydrophilic poly(vinyl alcohol) shell enveloping such surfaces while retaining the complex geometric configuration of the porous supporting structure. The method continues with the loading of the enzyme system in a water-miscible solvent system which wets the hydrophilic shell on such surfaces and the drying of the solvent to form a layer of the enzyme system on such surfaces.

The present invention also provides a method for loading an enzyme system in a water-miscible solvent on hydrophilic complex surfaces of a porous supporting structure without denaturing the enzyme system.

A feature of the invention is the ease of loading an enzyme system on all available surfaces of a hydrophilic porous supporting structure under minimally elevated temperatures and pressures without denaturing the enzyme system.

It is an advantage of the invention that hydrophilic porous supporting structures have surfaces which readily wet to accept both an enzyme system in a water-miscible solvent and any water needed for an enzyme catalyzed reaction.

It is another advantage of the invention that hydrophilic surfaces of the porous supporting structure, having a non-denatured enzyme system loaded thereon, provide reactive sites throughout all available surfaces of the structure.

It is another advantage of the invention that the enzyme system need not be in direct contact with moisture in the oxygen sensitive product being protected, as required by prior systems, because moisture can permeate into the pores of the hydrophilic surfaces of the porous structure.

For a greater appreciation of embodiments of the invention, a detailed description follows with reference to the drawing.

BRIEF DESCRIPTION OF THE DRAWING

FIG. 2a is a scanning electron photomicrograph of the outer and crosssectional surfaces of a polymeric structure made according to U.S. Pat. No. 4,539,256 without a tactic, hydrophilic poly(vinyl alcohol) shell thereon.

FIG. 2b is a scanning electron photomicrograph of the outer and crosssectional surfaces of a polymeric structure with a tactic, hydrophilic poly(vinyl alcohol) shell thereon made according to the present invention.

FIG. 3b is an exploded view of another illustration of the enveloped polymeric structure of FIG. 3a.

FIG. 4b is an illustration of an exploded view of the hydrophilic microstructure of FIG. 4a.

EMBODIMENTS OF THE INVENTION

Supporting Structure

Figure 1A:
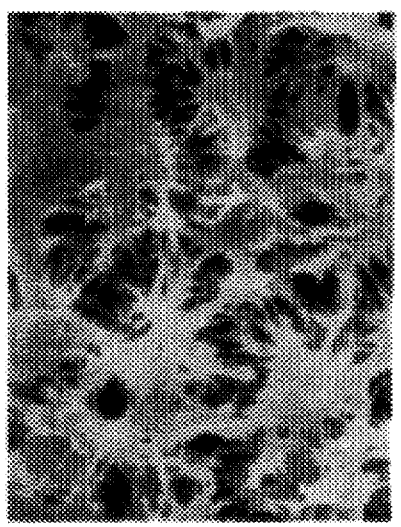
FIG. 1a is a scanning electron photomicrograph of the outer surfaces of a supporting structure made according to U.S. Pat. No. 4,539,256 without a tactic, hydrophilic poly (vinyl alcohol) shell thereon.

The supporting structure may be composed of any individual or combination of compositions of polymeric, ceramic, cellulosic, glassy, metallic, or carbonaceous materials. These materials may be either hydrophobic or hydrophilic in nature.

The supporting structure has a complex geometric configuration at a micron scale and may be formed according to known techniques into membranes, films, woven and nonwoven webs, beads, spun threads, porous fibers, porous hollow fibers, or any other three dimensional configuration having a topography which permits the poly(vinyl alcohol) shell to envelop surface(s) of the structure in a self-interlocking fashion.

Non-limiting examples of the types of surfaces which can be enveloped include reticulated porous microstructures and tentacular outer surfaces of a structure.

Desirably, surfaces of any of these supporting structures provide a greater surface area per unit mass than that apparent from the gross Euclidean dimensions of the supporting structure. Many uses of articles are dependent on providing a large surface area per unit mass. The hydrophilic polymeric shell of the present invention imparts hydrophilicity without reducing substantially the surface area of the supporting structure.

Polymeric structures are preferred supporting structures. Of polymeric structures, porous membranes are preferred. More preferably, these porous membranes are microporous.

The effective pore sizes of the structure may be at least several times the mean free path of flowing molecules, e.g., from about a nanometer to about several micrometers. The porous membrane has a reticulated surface structure throughout its mass, which provides surface(s) for enveloping the complex geometric configuration of the membrane with a tactic, hydrophilic, poly(vinyl alcohol) shell.

The polymeric structure may be made from any polymeric material which may be formed into a desired complex geometric configuration.

Non-limiting examples of the polymeric materials used to make polymeric structures are: polysulfones, polyethersulfones, poly(2,6-dimethyl-4-phenylene oxide) and derivatives thereof, polyamides, polyimides, polyetherimides, polyolefins, polyhalo olefins (especially polytetrafluoroethylene), polyesters, nylon, and the like.

Non-limiting examples of suitable polyolefins include (regardless of molecular weight) polyethylene, polypropylene, poly-3-methyl-1-butene, poly-4-methyl-1-pentene, copolymers of ethylene, propylene, 3-methyl-1-butene, or 4-methyl-1-pentene with each other or with minor amounts of other olefins, e.g., copolymers of ethylene and propylene, copolymers of a major amount of 3-methyl-I 1-butene, and a minor amount of a straight chain n-alkene having from 2 to 18 carbon atoms such as 1-octene, 1-hexadecene, and octadecene or other relatively long chain alkenes, as well as copolymers of 3-methyl-1-pentene, and any of the same alkenes mentioned previously in connection with 3-methyl-1-butene.

A polyolefinic material may also include small amounts of other materials which may be copolymerized or blended therewith, but which do not substantially adversely affect the characteristics of the polyolefinic material.

The material comprising the polymeric structure should have a weight average molecular weight greater than about 1000, and preferably greater than about 50,000, a melt index less than about 1200 grams/10 minutes and preferably less than about 10 grams/10 minutes as measured according to ASTM D1238-82.

When the polymeric structure takes the form of a porous or microporous membrane or other porous configuration, the polymeric structure should have a porosity of from about 15 percent to about 99 percent, and preferably from about 30 percent to about 95 percent. The porosity measurements are made according to ASTM D-792.

When the polymeric structure takes the form of a membrane or other porous configuration, the structure should have an effective pore size in micrometers, measured according to ASTM F-316, of from about 0.01 µm to about 20 µm, and preferably from about 0.1 µm to about 1.2 µm.

Tactic, Hydrophilic Poly(vinyl Alcohol) Shell

The tactic, hydrophilic poly(vinyl alcohol) is prepared by the reaction of a tactic, polymeric poly(vinyl alcohol) precursor with a hydrolysis reagent. The tacticity of the poly(vinyl alcohol) ranges from about 50 percent tactic triads to about 80 percent tactic triads using Fluorine NMR spectroscopy methods. Pritchard et al., "Fluorine NMR Spectra of Poly(vinyl Trifluoroacetate)" J. Poly. Sci. 4, 707–712 (1966), incorporated by reference herein, discloses calculation of triad tacticities for poly(vinyl alcohol) prepared by various methods.

The extremely thin shell of poly(vinyl alcohol) enveloping surface(s) of a supporting structure is described in terms of monolayers of poly(vinyl alcohol) on complex surfaces of a supporting structure. A "monolayer" is the thickness of the smallest dimension of a crystalline unit cell of poly(vinyl alcohol), about 2.53 Angstroms. The poly(vinyl alcohol) shell may comprise greater than an average of 10 monolayers to impart hydrophilicity to the complex geometric and often hydrophobic surfaces of a supporting structure.

The "extremely thin" self-interlocking shell of poly(vinyl alcohol) imparting hydrophilicity does not appreciably swell upon exposure to water to substantially alter the complex geometric configuration of a supporting structure.

Reference to an "average of" a number of monolayers compensates for the fact that these extremely thin shells are not of exact uniform thickness throughout the entire complex geometric configuration of the supporting structure.

If the supporting structure is porous and it is desired not to block or clog such pores of a nominal 2 micron pore size, the poly(vinyl alcohol) shell may comprise from about an average of about 10 to about 4,000 monolayers. Desirably, the poly(vinyl alcohol) shell may comprise from about an average of 10 to about an average of 400 monolayers. It is presently preferred that the poly(vinyl alcohol) may comprise from about an average of 10 to about an average of 40 monolayers.

Based on the dimensions of pore size of a porous supporting structure and the monolayers of poly(vinyl alcohol) enveloping surfaces of that supporting structure, it is desirable to have a shell of tactic poly(vinyl alcohol) occupy less than 30 percent of the pore size existing in the supporting structure prior to forming such poly(vinyl alcohol) shell. Preferably, the tactic poly(vinyl alcohol) occupies less than 15 percent of the original pore size.

The tactic, hydrophilic poly(vinyl alcohol) shell is relatively insoluble in water or highly polar organic solvents, or nonpolar organic solvents. Such organic solvents include without limitation, dimethylsulfoxide, glycerol, ethylene glycol, and other solvents having a solubility parameter differential from poly(vinyl alcohol) of greater than about 0.4 and desirably greater than about 0.6. The solubility parameter δ (H) for poly(vinyl alcohol) is about 12.6. A tactic poly(vinyl alcohol) shell of the present invention resists some washings by solvents having solubility parameters of less than about 12.2 or greater than about 13.0. Moreover, the tactic poly(vinyl alcohol) shell resists repeated washings by solvents having solubility parameters of less than about 12.0 or greater than about 13.2. Solubility parameters for solvents may be found in the *Handbook of Chemistry and Physics*, 60th Edition, Chemical Rubber Company. The tactic, hydrophilic poly(vinyl alcohol) shell of the present invention resists washout by any of the above-named solvents.

Desirably, the initial solubility of the hydrophilic poly (vinyl alcohol) shell when exposed to the above-named solvents is less than about 1 part per 100 parts of solvent at room temperatures and pressures with no measurable solubilization thereafter. Such relative insolubility of the poly (vinyl alcohol) shell in water and polar and nonpolar organic solvents provides continuing hydrophilicity of the article during usage in the presence of such solvents.

Polymeric Poly(vinyl Alcohol) Precursor

The poly(vinyl alcohol) precursor may be a tactic homopolymer of vinyltrifluoroacetate, a tactic copolymer of vinyltrifluoroacetate monomer and monomer(s) having a vinylic group therein, a tactic homopolymer of vinyl tert-butyl ether, or a tactic copolymer of vinyl tert-butyl ether monomer and monomer(s) having a vinylic group therein.

The weight average molecular weight of the homopolymer or copolymers of poly(vinyltrifluoroacetate) range from about 50,000 to about 2,000,000 and desirably range from about 500,000 to about 1,000,000. Desirably, the syndiotactic homopolymer or syndiotactic copolymer of poly (vinyltrifluoroacetate) is unbranched.

The weight average molecular weight of the homopolymer or copolymers of poly(vinyl tert-butyl ether) range from about 25,000 to about 60,000 and desirably from about 35,000 to about 45,000.

Non-limiting examples of monomers having a vinylic group therein, useful for copolymerization to form the precursor, include vinyl esters having up to six carbon atoms, vinyl ethers having up to eight carbon atoms, and disubstituted ethylenes (such as esters or anhydrides of lower alkyl ($C_1$–$C_4$) substituted or unsubstituted dicarboxylic acids having up to eight carbon atoms). Of these possible monomers, maleic anhydride and vinyl acetate are preferred.

The presently preferred precursor is syndiotactic poly (vinyl trifluoroacetate) homopolymer.

The precursor typically is hydrophobic and is applied in relatively dilute solution. The solvent may be any liquid that wets the surfaces of the supporting structure and solubilizes the precursor.

A solvent which allows spontaneous wetting of the precursor solution on all available surfaces of a hydrophobic supporting structure is preferred. The term "all available surfaces" includes without limitation, the reticulated pores and interstices of a porous hydrophobic article or the tentacular surface of a film, bead or web. Spontaneous wetting provides rapid, even envelopment of all of the available internal and external surfaces of the article, and an application of at least an average of 10 monolayers thickness of the precursor on such surfaces for further processing. It is possible for a porous supporting structure to have some pores having radii smaller than the hydrodynamic radius of the precursor. The surfaces along such smaller pores may not be available for application of the precursor, because the precursor molecule is too big to enter the pore.

The concentration of the precursor in solution determines the ability of the precursor to cover all available surfaces of the supporting structure while substantially retaining the complex geometric configuration of the supporting structure. The concentration of the precursor in the solvent may range from about 0.5 percent (w/v) to about 15 percent (w/v). Desirably, the concentration ranges from about 2 percent (w/v) to about 10 percent (w/v). Preferably, the concentration ranges from about 3 percent (w/v) to about 8 percent (w/v).

The solvent is desirably organic and has a significant vapor pressure at a temperature of less than about 38° C.

When the supporting structure is hydrophobic, the solvent may be any liquid which solubilizes the precursor and wets the supporting structures' surfaces. Nonlimiting examples include: ketones, esters, ethers, nitrites, or amides having aliphatic, alicyclic, or aromatic groups. Of these solvents, acetone, ethyl acetate, cyclohexanone, tetrahydrofuran, pyridine, acetophenone, and acetonitrile are desired. Of these solvents, acetone is preferred due to its availability, cost, and handling.

Hydrolysis Reagent

The hydrophobic polymeric poly(vinyl alcohol) precursor applied to the surfaces of the supporting structure is converted, in-situ, to tactic poly(vinyl alcohol) by a hydrolysis reagent which is capable of converting the pendant trifluoroacetate groups of the precursor into hydroxyl groups. The hydrolysis reagent may be applied in either a liquid or a gaseous state. The hydrolysis reagent may be acidic or basic, but desirably it is basic. Thus, a desirable hydrolysis reagent has a pH of greater than about 7.0 and desirably from about 8 to about 10.

Non-limiting examples of a hydrolysis reagent include sodium hydroxide in methanol, sodium carbonate in a methanol/water solution, ammonium hydroxide in methanol, potassium hydroxide in a methanol/water mixture, and aqueous or vaporous ammonia. Of these reagents, ammonia is preferred in the vapor phase or in a methanol/water mixture.

When vaporous ammonia is used, it is presently preferred to hydrate the surfaces of the supporting structure and the shell of tactic poly(vinyl alcohol) with water or moisture vapor to stabilize hydrophilicity of the shell. Otherwise, it is possible for the extremely thin shell of poly(vinyl alcohol) to conformationally rearrange, causing loss of some or a substantial portion of hydrophilicity, if such article is not placed into use in aqueous-based solvents within weeks after manufacture of the hydrophilic article.

The amount of contact between the hydrolysis reagent and the precursor should be sufficient in duration and in concentration to permit complete conversion of the tactic precursor to tactic poly(vinyl alcohol). Desirably, the polymeric supporting structure having the precursor applied to its surfaces is immersed in a solution containing the hydrolysis reagent having a pH of greater than 7.0.

Method To Make The Article

The manufacture of an article having a hydrophilic polymeric shell varies according to its composition and its ultimate shape.

The supporting structure may be formed from commercially available materials depending on form and composition desired by those skilled in the art.

Raw materials suitable as base materials for supporting structures are commercially available. For example, polymeric supporting structures may be prepared from commercially available resins using a variety of extrusion, membrane preparation, or film-forming techniques well known in the art. A preferred method of membrane preparation is disclosed in U.S. Pat. No. 4,539,256, the disclosure of which is incorporated by reference herein.

Membranes of polysulfone are commercially available from Schleider and Schuell of Keene, N.H. Polyolefinic microporous membranes are commercially available from Hoeschst-Celanese of Charlotte, N.C. and references to the methods of manufacture of such polyolefinic microporous membranes may be found in U.S. Pat. Nos. 4,501,793 and 3,853,601, both of which are incorporated by reference herein.

For the poly(vinyl alcohol) precursor, a poly(vinyl trifluoroacetate) homopolymer may be made according to U.S. Pat. No. 2,436,144, incorporated by reference herein. A poly(vinyl trifluoroacetate) copolymer may be made according to U.S. Pat. No. 2,436,144 or according to co-assigned U.S. Pat. Nos. 4,528,325, and 4,618,649, both of which are incorporated by reference herein.

Vinyltrifluoroacetate and comonomers for synthesis of poly(vinyltrifluoroacetate) are commercially available from Polysciences of Warrington, Pa. and Aldrich Chemical of Milwaukee, Wisc.

A solution of tactic, poly(vinyl alcohol) precursor in a solvent which wets the supporting structure is then applied onto all available surfaces of the supporting structure, saturating the complex surfaces. Upon evaporation of the solvent, a self-interlocking shell is formed which substantially retains the complex geometric configuration of the structure.

Depending upon the configuration of the supporting structure and its composition, the method of application of precursor solution may involve wiping, dipping, rolling, knifing or extruding steps as the case permits. The solvent may be removed by drying the polymeric shell for such times and at such temperatures and pressures to fully dry the precursor. Processing conditions may be controlled as necessary to permit drying of the precursor on surfaces without covering or clogging available porous surfaces of the supporting structure. The application of precursor may occur batch-wise or continuously according to the manufacturing processing conditions preferred.

For example, to prepare an unclogged porous membrane, the in-situ conversion of tactic precursor to tactic, hydrophilic poly(vinyl alcohol) occurs by hydrolysis at less than about 38° C. using a hydrolysis reagent in either liquid or vaporous phase. A closed reaction vessel for vaporous reaction is preferred. A dipping tank for liquid reaction is preferred.

When ammonia vapor is used, after a closed vessel is employed, the membrane is dipped or sprayed with water or moisture vapor to lock in hydrophilicity of the poly(vinyl alcohol) shell.

While it is preferable to provide hydrophilic surfaces for the supporting structure, it can be desirable in certain articles to be able to reverse hydrophilicity into hydrophobicity after a process step or other intermediate activity. Hydrophilic shells of poly(vinyl alcohol) of the present invention can be conformationally rearranged into hydrophobic surfaces by heating the hydrophilic supporting structure above the glass transition temperature (Tg) of poly(vinyl alcohol), about 80 degrees C., for a limited period of time. Without being limited to a particular theory, it is believed that the increased mobility of poly(vinyl alcohol), above its Tg, allows a conformational rearrangement of hydroxyl groups at outer surfaces of the shell to point in towards the bulk of the shell. The driving force for this rearrangement is a natural desire to minimize interfacial energy (i.e., between the shell surface and air). This results in the outermost few Angstroms of the shell surface being defined by the hydrocarbon backbone of the poly(vinyl alcohol). Since "wetting" and hydrophilicity is defined by the outermost few Angstroms of a surface, the presence of the hydrocarbon backbone in place of hydroxyl groups results in the surface no longer being hydrophilic. Thus, the shell has the same chemistry but is hydrophobic.

Hydrophobic poly(vinyl alcohol) can be converted to hydrophilic poly(vinyl alcohol) by wetting surfaces of the shell-covered supporting structure with a polar, water-miscible solvent, such as methanol or acetone, followed by solvent exchanging water into pores of the supporting structure and drying. In such re-hydrophilization, contact of a poly(vinyl alcohol) shell with such polar, water miscible solvent re-orients hydroxyl groups out from such surfaces. Water or moisture vapor plasticizes poly(vinyl alcohol), swells such shell, and lowers the glass transition temperature thereof in the presence of such a polar environment.

Thus, according to methods of the present invention, one can control hydrophilization of supporting structures, throughout all surfaces, only at outer surfaces, or only in pores or interstices. One can create regio-specific hydrophilic surfaces for a supporting structure according to need. Non-limiting examples of such regio-specific surfaces can be patterned hydrophilicity throughout specific portions of a porous membrane, "facade" hydrophilicity of a porous membrane, or a "sandwich" hydrophilicity having hydrophobic inner pores and interstices.

Alternatively, regio-specific hydrophilization can be achieved by introducing a hydrolysis reagent only to designated portions of surfaces of a supporting structure covered with polymeric poly(vinyl alcohol) precursor. Also, such regio-specific hydrophilization can be achieved by applying polymeric poly(vinyl alcohol) precursor to designated portions of surfaces of the supporting structure, followed by hydrolysis of such portions with hydrolysis reagent.

However, some uses of the article may prefer skinned, covered or clogged pores, to convert a fractal geometric configuration of the article to a Euclidean geometric configuration. In such circumstances, processing conditions or solutions may be adjusted as desired. Three parameters may be adjusted. Choice of solvent influences rate of coverage and evaporation. Precursor concentration determines solution viscosity, rate of pore penetration, and shell thickness. Pore sizes of surfaces of the article also determine rate of pore penetration.

Figure 1B:
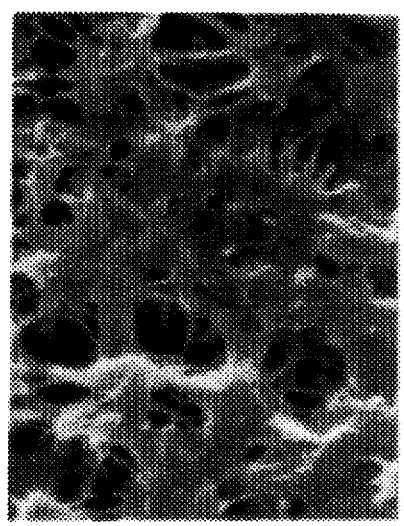
FIG. 1b is a scanning electron photomicrograph of the outer surfaces of a supporting structure with a tactic, hydrophilic poly(vinyl alcohol) shell thereon made according to the present invention.

FIG. 1 illustrates the comparison between a hydrophobic microporous membrane (prepared according to Example 23 of U.S. Pat. No. 4,539,256) and a microporous membrane having with tactic, hydrophilic poly(vinyl alcohol) shell (prepared according to the present invention). The outer surfaces of the article in scanning electron photomicrograph 1a are hydrophobic and untreated. The outer surfaces shown in scanning electron photomicrograph 1b are hydrophilic due to the tactic, hydrophilic poly(vinyl alcohol) shell about its surfaces. The treated membrane shown in scanning electron photomicrograph 1b retains its fractal geometric configuration because its complex surfaces are substantially as open and unclogged as the unprocessed membrane in photomicrograph 1a. Thus, the pores and interstices of supporting structure are not filled or occluded by the in-situ generated poly(vinyl alcohol) shell. The fractal configuration of the supporting structure is not converted to a Euclidean configuration. Thus, the membrane retains its structural advantages while adding hydrophilic surfaces.

FIG. 2 illustrates that a microporous membrane having a tactic, hydrophilic poly(vinyl alcohol) shell enveloping both outer and inner porous surfaces of the membrane does not clog or occlude any pores or interstices. Scanning electron photomicrograph 2a of the same hydrophobic membrane as in FIG. 1a and scanning electron photomicrograph 2b of the same hydrophilic membrane as in FIG. 1b both show about 10 microns of cross-section of the membrane at the bottom of the scanning electron photomicrographs, with the remainder being a perspective view of the outer surface. No significant difference can be seen between these two photos.

Figure 3A:
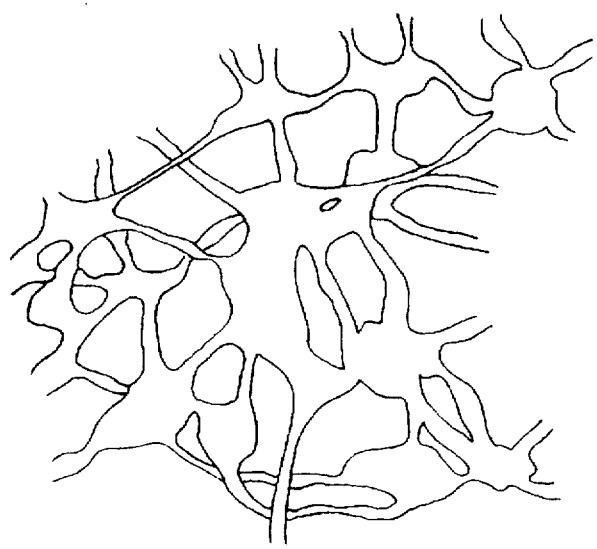
FIG. 3a is an illustration of a membrane microstructure which is enveloped by a poly(vinyl alcohol) shell.
Figure 3B:

While not being limited to any particular theory, it is believed that the shell of tactic poly(vinyl alcohol) envelops available surfaces of the supporting structure by forming tie molecules among crystallite molecules. FIG. 3a illustrates a membrane microstructure which is enveloped by a poly (vinyl alcohol) shell. The exploded view of FIG. 3b provides another illustration of the enveloped polymeric structure. Tie molecules of poly(vinyl alcohol), such as those described in Basset, D.C., *Principles of Polymer Morphology*, Cambridge Univ. Press, 1981, between crystallites of poly(vinyl alcohol), provide the self-interlocking strength of the shell. The complex geometric configuration of the underlying polymeric structure is substantially retained after envelopment of from about an average of 10 to about an average of 4000 monolayers of poly(vinyl alcohol) and desirably from about an average of 10 to about an average of 400 monolayers of poly(vinyl alcohol).

Usefulness Of The Invention

The hydrophilic supporting structures of the present invention can be utilized in several applications involving aqueous fluids or hydrophilic organic solvents. The chemical inertness and complex geometric configuration of many hydrophobic materials or structurally weak hydrophilic materials would make them ideally suited for hydrophilic processes if the supporting structure had hydrophilic surfaces of a self-interlocking shell.

Having a tactic, hydrophilic poly(vinyl alcohol) shell enveloping surfaces of such hydrophobic supporting structures enables such structures to be used in aqueous systems or in hydrophilic organic solvents in which the untreated supporting structure above would be inadequate, incompatible, or ineffective, notwithstanding its complex geometric configuration desired for such mechanical processes. The relative insolubility of the tactic, hydrophilic poly(vinyl alcohol) shell in a large number of organic solvents and water enables the article to be used in those circumstances where the solvent must wet the article in order for the article to perform its intended purpose. A useful measure of "wetting" capability is pore wetting surface energy.

"Pore wetting surface energy" means the surface energy of the supporting structure required for spontaneous wetting of a pore through the wicking of water into the pore via capillary forces. Spontaneous wetting of the pore occurs when the surface energy of the internal surface of the pores is high enough for water to have less than a 90° contact angle with the surface. Analytically, according to Wu, S., *Polymer Interface and Adhesion*, Marcel Dekker, New York, 1982, p. 244, spontaneous wetting occurs when the capillary force, $\Delta P_c$, in the following equation is positive:

$$\Delta P_c = 2\sigma_L \cos\Theta / r$$

where $\sigma_L$ is liquid surface tension (72.8 dynes/cm for water), $\Theta$ is the contact angle (<90°), and r is the pore radius.

The magnitude of the positive capillary force correlates to the rate of spontaneous wetting. The variation in pore size and complex geometric configuration also assists in controlling the rate of migration.

The tactic, hydrophilic poly(vinyl alcohol) shell enveloping the supporting structure also provides the advantage of increasing the mechanical strength of a supporting structure. By enveloping internal and external surfaces of a membrane while substantially retaining the complex geometric configuration of the membrane (e.g., a microporous membrane having pore sizes of from about 0.01 μm to about 1.2 μm,) the tactic poly(vinyl alcohol) shell increases the tensile strength and percent elongation properties of the supporting structure. While not limited by any particular theory, it is believed that the enhanced tensile strength is achieved by the covering of acute geometric interstices of the fibrillar structure which would otherwise be probable stress concentration points for failure initiation in the complex geometric configuration. While acute geometric intensities may be lessened, the overall complex geometric configuration is substantially retained.

The presence of a tactic, hydrophilic poly(vinyl alcohol) shell about a supporting structure provides highly reactive hydroxyl sites for further chemical, physical, and biological uses.

The present invention has broad utility in that articles having durable hydrophilic polymeric shells can be prepared from a wide variety of supporting structure materials which can comprise any of several compositions and take any of several forms. The present invention's ability to provide articles having a non-crosslinked self-interlocking shell comprising hydroxyl functionality that displays minimal solubility in water and aqueously soluble organic solvents provides advantages not previously found in the art.

Oxygen Scavengers

Hydrophilic porous supporting structures have considerable usage as reservoirs for enzyme systems. The enzyme system in a water-miscible solvent system is typically loaded on the surfaces of the hydrophilic shell of the porous supporting structure throughout the complex geometric configuration of the porous supporting structure.

The supporting structure may be composed of any individual or combination of supporting structures described in these Embodiments of the Invention and which are polymeric, ceramic, cellulosic, glassy, metallic, or carbonaceous porous materials. These porous materials may be either hydrophobic or hydrophilic in nature.

Enzyme Systems

Nonlimiting examples of enzyme systems include glucose oxidase; a glucose/glucose oxidase combination; a glucose oxidase/sucrose combination; a starch/amylase/glucose oxidase combination; a cellulose/cellulase/glucose oxidase combination; a milk powder/lactase/glucose oxidase combination; a glucose oxidase/fructose isomerase/fructose combination; a glucose oxidase/lactase/whey solids/lactose combination; a glucose/lactase/lactose combination; a glucose oxidase/maltase/starch combination; a glucose oxidase/maltase/maltose combination; a mushroom tyrosinase/tyrosine combination; a glucose oxidase/sucrose/sucrase combination; and any combination of Ebden-Meyerhoff-Citric Acid cycle enzymes.

Typically the enzyme system is processed in a water-miscible solvent system, such as an aqueous buffer system. The water-miscible solvent wets the hydrophilic surfaces of the porous supporting structure and delivers the enzyme system to all available surfaces of the hydrophilic porous supporting structure.

Of the preceding illustrative examples, a 50% (W/V) dextrose/citrate buffer solution (having a pH of 6.3) containing glucose oxidase enzyme in a concentration of 2.5 mg/ml and having a "Finnsugar stated activity" of 110 units/mg is presently preferred for loading on a hydrophilic porous supporting structure. "Finnsugar stated activity" is determined by AP0002, Revision F of Glucose oxidase, titrimetric assay published in 1988 by Finnsugar Biochemicals, Inc. of Schaumberg, Ill., the disclosure of which is incorporated by reference herein.

Nonlimiting examples of loading the enzyme system onto the hydrophilic porous supporting structure include soaking, wiping, dipping, rolling, spraying, or knifing. Drying at ambient temperatures and pressures or slightly elevated temperatures not exceeding approximately 70° C. permits the evaporation of the water-miscible solvent system without deleteriously affecting or inactivating the enzyme loaded on the surfaces of the hydrophilic porous structure. Alternatively, drying may occur at higher temperatures if there is a highly convective air flow about the porous supporting structure.

Enzyme-loaded Hydrophilic Porous Supporting Structures

Figure 4A:
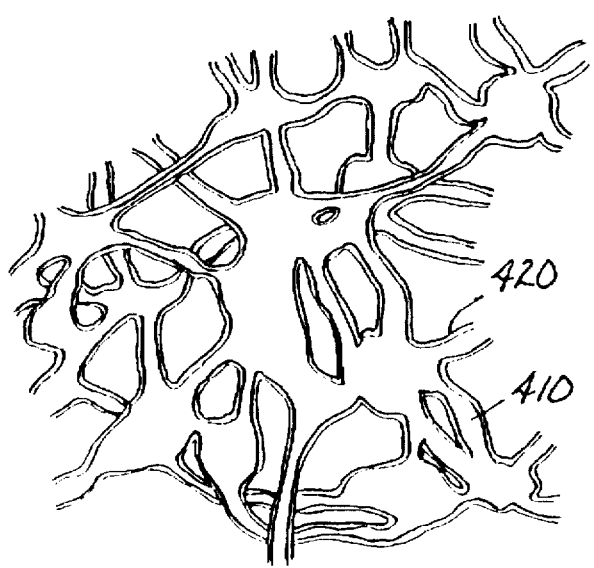
FIG. 4a is an illustration of a hydrophilic membrane microstructure with an enzyme system loaded thereon.
Figure 4B:
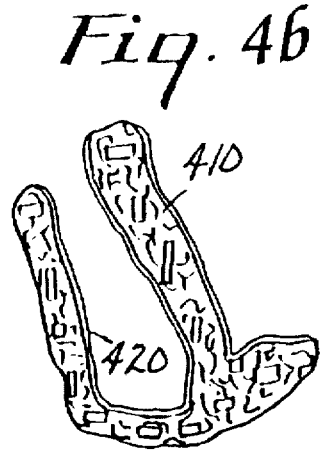

As seen in FIG. 4, the hydrophilic membrane 410 has a layer of enzyme system 420 loaded on the poly(vinyl alcohol) shell enveloping the complex geometric configuration of the porous supporting structure. The layer of enzyme system is loaded on all available hydrophilic surfaces of the porous supporting structure because the hydrophilic shell permits the wetting of such surfaces by a water-miscible solvent system containing the enzyme system.

The layer 420 of enzyme system forms, without a binder needed, on the hydrophilic surfaces of the membrane 410 as the water-miscible solvent evaporates. The thickness of the layer must be at least a minimally useful thickness. Because the hydrophilic shell does not denature the enzyme system, substantially all of the enzyme system forming a layer remains active for oxygen scavenging.

Desirably, the layer 420 of enzyme system is sufficiently thin to avoid blocking, clogging, or skinning the pores of the supporting structure. Thus, for a porous structure having a pore size of about an average of 0.5 µm, the layer 420 of enzyme system does not exceed about 0.075 µm.

Preferably, the porous supporting structure does not lose more than about 60% of its pore size due to the formation of the hydrophilic shell and the loading of the enzymatically active material thereon. Thus, for a porous supporting structure having a pore size of an average of 0.5 µm, the layer 420 of enzyme system does not exceed about 0.15 µm in thickness. As seen in FIG. 4a, the layer 420 is illustrated as having the presently preferred thickness relative to the monolayer thickness of the hydrophilic membrane 410 and the pore size shown.

The enzyme system protects oxygen sensitive products from deleterious interaction with molecular oxygen, whether the molecular oxygen is in the headspace of a container at the time of packaging or enters the packaging thereafter. Even within an enclosed area, an oxygen sensitive product may have a limited shelf life due to its reactivity with oxygen in the headspace of the container.

Nonlimiting examples of oxygen sensitive products which may be protected by the present invention include natural and processed food products such as cheese, luncheon meats, bacon, fermented dairy products, fruits and vegetables, raw meats, poultry, fresh and salted fish, intermediate moisture foods (such as jerky, pet foods, and granola bars), high fat moist bakery products, acidified dairy products, mayonnaise and salad dressings, controlled atmosphere/modified atmosphere refrigerated extended shelf life foods (such as partially cooked meals, pasta dishes, sauces, cut fruit, and vegetable salads, and other water-bearing foods.

Because the enzyme system is loaded on all available surfaces of the hydrophilic porous structure, and because water or moisture may penetrate the hydrophilic porous structure, an enzyme-catalyzed reaction may occur throughout the porous structure. The enzyme-loaded porous structure need not necessarily be in contact with an oxygen sensitive product. Thus, the enzyme-loaded porous structure may be a liner or pad, either inside the cap or lid at the top of the headspace of a container or along any portion of the interior of the package within or beyond contact with the oxygen sensitive product.

The oxygen sensitive product may be enclosed in a package with the enzyme-loaded hydrophilic porous structure within the package. Molecular oxygen, both remaining in the package at the time of packaging and entering the package after packaging is scavenged by operation of the enzyme system. The enzyme catalyzed reaction of a substrate, oxygen, and if necessary, water forms byproducts and consumes oxygen. With the porosity of the supporting structure substantially retained, the flow of oxygen and water or moisture within the package may pass through the enzyme-loaded, porous supporting structure.

If the enzyme system includes the substrate, the enzyme-catalyzed reaction can occur at all available surfaces of the structure. Because water readily penetrates the hydrophilic porous structure, vastly more interior surface area is available for the oxygen consuming reaction than just at the exterior surfaces of the structure.

The form of the porous structure is not limited to liners or pads but may take any of the forms described above. When loaded with an enzyme system, any of those forms may be used for oxygen scavenging.

So long as the oxygen sensitive product is not adversely affected by the presence of a substrate or reaction byproducts in the package, the product's shelf life is improved by the consumption of oxygen before reaction with the oxygen sensitive product.

Some catalyzed reactions may generate hydrogen peroxide as a byproduct. The released hydrogen peroxide may be of some benefit to extend shelf life of meats, poultry and fish if the hydrogen peroxide is in direct contact with the wet surfaces of those foods. Alternatively, concern about the generation of hydrogen peroxide may be minimized by including catalase in the enzyme system. The catalase converts hydrogen peroxide into water and oxygen, which are further reacted with substrate in the presence of the enzyme until the cycle effectively consumes oxygen in the package from all sources.

While a planar surface not having a complex geometric configuration may have a layer of the enzyme system placed thereon and perform an oxygen scavenging function within a package, the surface area available for immobilizing the enzyme system and for providing reactive sites for oxygen scavenging is much more limited. For example, monolayer coverage of an enzyme system on a non-porous structure provides only about 0.1 µg/cm$^2$ of enzyme, whereas adequate enzyme coverage for practical oxygen scavenging requires a minimum of about 3 µg/cm$^2$ of enzyme. Thus, it is not possible to achieve a practical oxygen consumption using an enzyme system on a flat film. However, a porous supporting structure having a complex geometric configuration does achieve adequate oxygen scavenging because of the extremely large surface area/exterior surface area ratio. For example, a 100 µm thick membrane having a 20 m$^2$/gm$^2$ surface area provides about 600 times the surface area as one side of a 1 cm$^2$ surface of a flat film. Thus, a porous supporting structure having a complex geometric configuration can have at least 600 times as much enzyme system loaded on its porous surfaces.

Other materials may be added to a package containing the enzyme-loaded porous structure of the present invention. Nonlimiting examples include adding a second material having additional amounts of the same or a different substrate into the package, preferably in a contiguous position to the enzyme-loaded porous structure. In general, because the enzyme is a catalyst and the substrate is converted to a byproduct in the oxygen scavenging process, the greater the amount of substrate in the package, the greater the amount of oxygen which may be consumed.

This invention is not limited to the embodiments described here or by the examples which follow.

EXAMPLES

In the examples to follow, certain tests were conducted and are described below:

Gurley Value—This value is a measurement of time in seconds to pass 50 cm$^3$ of air through a porous film according to ASTM D-726, Method A.

Bubble Point Pore Size—This is a measurement of the maximum effective pore size, in microns, according to ASTM F-316. This value is also referred to as "pore size" in the Examples.

Porosity—This is a measure of the void volume of the porous article, and is derived from the measurement of specific gravity of the article, according to ASTM D-792. The porosity is defined as:

$$\text{Porosity} = \left(1 - \frac{\text{bulk density}}{\text{polymer density}}\right) \times 100$$

Tensile Strength—Values measured according to ASTM D 638-80 using an Instron model 1122 tensile tester under the following conditions:

| Jaw Gap: | 5.08 cm |
| --- | --- |
| Jaw Speed: | 50.8 cm/min |
| Sample Size: | 2.54 cm wide strip |

MD and TD values for the tensile strength refer to measurements made in the "machine direction" and the "transverse direction" respectively.

Water Permeability—Water permeability was determined by placing a 74 mm diameter piece of the membrane in a test cell, which used an o-ring to seal the membrane to a sintered stainless steel back-up plate. The cell was equipped with a 350 ml water reservoir and was pressured with compressed nitrogen. The water flow rate was calculated by measuring the volume of water passed through the sample in a given time, with a 10 psi (or 68.947 N/M$^2$) head pressure. At least three measurements were averaged for each permeability value reported.

Example 1

Preparation of the poly(vinyl alcohol) precursor, syndiotactic poly(vinyl trifluoroacetate), was performed in a one gallon glass bowl jacketed pressure reactor having a stainless steel lid fitted with a metal turbine agitator blade on a sealed shaft, two mixing vanes, a thermowell and at least two valved openings. The system was purged with a sweep of dried argon to remove moisture and oxygen before adding reactants or solvent. Materials were weighed and transferred in closed vessels under inert gas and anhydrous conditions. Charges were made through rubber septa covering the opened valves in the reactor lid using proper techniques to prevent uptake of atmospheric moisture and oxygen. Into the reactor were placed, in order, 3025 g of Freon 113, 17.5 ml of a premix containing 2.5 g of trifluoroacetic anhydride in 25 ml of Freon 113, 355 g vinyl trifluoroacetate monomer, 14 ml of a second premix containing 2.5 g of bis(4-t-butylcyclohexyl) peroxydicarbonate (commercially available as "Percadox" 16N from Akzo Chemie America, Noury Chemicals of Chicago, Ill.) in 25 ml of Freon 113. The reactor temperature was raised to 45° C. and maintained at that temperature for about 18 hours with an agitator speed at about 1000 rpm. A slight exotherm was observed during the reaction with a maximum system pressure of about 10–12 psig (0.7–0.8 kg/cm$^2$). The polymerized, syndiotactic poly (vinyl trifluoroacetate) (PVTFA) was isolated by filtration and dried at 40° C. under vacuum overnight.

A microporous polyethylene (PE) membrane, made by thermally induced phase separation as disclosed in Example 23 of U.S. Pat. No. 4,539,256 (Shipman) the disclosure of which is incorporated herein by reference, having a maximum pore size of 0.5 micron, a porosity of 81.5 percent and a thickness of 0.074 mm, was saturation treated with a 4 percent (w/v) acetone solution of PVTFA using an extrusion die. The membrane was dried slowly for 1.6 minutes in a two zone air floatation oven with the two zones set at temperatures of 27° C. and 38° C. respectively, resulting in a 22.2 weight percent add on of the PVTFA shell formed on the external and internal pore surfaces. No substantial blocking of the pores occurred, nor was a PVTFA skin formed on the covered side as evidenced from scanning electron microscopy (SEM) analysis. The complex geometric configuration of the membrane was substantially retained. Bubble point measurements showed a reduction in the maximum pore size to 0.44 micron.

A piece of this dry membrane was placed in an ammonia-saturated glass vessel for 2 minutes in order to convert, in-situ, the PVTFA shell to a poly(vinyl alcohol) (PVA) shell. The ammonia atmosphere was generated by placing a concentrated ammonium hydroxide solution in the bottom of the vessel. A 68 weight percent reduction in the weight of the shell resulted from the hydrolysis reaction.

Fourier Transform Infrared, (FT-IR), spectroscopy (at 4 cm$^{-1}$ resolution, 64 scans, between a range of 4000 cm$^{-1}$ and 400 cm$^{-1}$, through the membrane) confirmed that the 68 weight percent loss in shell weight, which occurred during this basic hydrolysis reaction step was due to the quantitative loss of the trifluoroacetate group from the PVTFA. This amount of weight loss corresponded exactly to the amount of weight loss expected for 100% conversion from PVTFA to PVA. Upon removing the membrane from the ammonia atmosphere, it displayed spontaneous and nearly instantaneous wetting with water. The complex geometric configuration of the membrane was substantially retained throughout the hydrolysis treatment as was evidenced by a pore size loss of less than eight percent.

The ability of the hydrophilic membrane to resist washout of the PVA shell by common organic solvents was demonstrated by soaking pieces of the membrane in large amounts of acetone, isopropyl alcohol, and 1,1,1-trichloroethane. After 45 minutes of soaking in each of these solvents, the re-dried membranes retained their hydrophilicity, as shown by their spontaneous and nearly instantaneous wetting with water. The ability of the hydrophilic membrane to resist wash-out of the PVA shell by water was demonstrated by passing 2000 ml of deionized water through a 36 cm$^2$ piece of this membrane. After drying, the hydrophilicity of the membrane remained unchanged (i.e., it was spontaneously and nearly instantly wetted with water).

The porous properties of the starting PE microporous membrane, the PVTFA covered membrane, and the final PVA shell hydrophilic membrane are reported in Table 1 below.

TABLE 1

| Membrane | Coating Weight | Thickness | Pore Size | Percent Pore Size Loss | Porosity | Gurley | Water Permeability* |
|---|---|---|---|---|---|---|---|
| PE | — | 0.074 mm | 0.496 µ | — | 81.5% | 9.4 sec | 0** |
| PVTFA covered PE | 22.2% | 0.056 mm | 0.438 µ | 12% | 73.2% | 17.6 sec | 0** |
| PVA shelled PE | 8.4% | 0.056 mm | 0.436 µ | 7% | 73.6% | 15.2 sec | 0.052 L/(m$^2$*hr*Pascals) |

*Water permeability measured at 68,930 Pascals (10 psi).
**No flow of water occurs at 68.930 Pascals through this hydrophobic membrane without an ethanol pre-wetting step due to the hydrophobicity of PE and PVTFA. When measured after ethanol pre-wetting and a solvent exchange of water, PE Water Permeability measured 0.043 and PVFTA coated PE Water Permeability measured 0.033 L/m$^2$*hr*Pascal), respectively.

Example 2

A hydrophilic membrane was prepared according to the procedure of Example 1 except that the syndiotactic PVTFA solution was applied to the membrane using a #8 wire-wound bar to spread the PVTFA solution on the membrane. The sample was allowed to dry at room temperature in a ventilation hood to produce a PVTFA treated membrane without causing pore blockage or PVTFA skin formation as shown by SEM examination. The PVTFA treated membrane retained the complex geometric configuration of the starting membrane. The sample was reacted with vaporous ammonia as in Example 1 to yield a hydrophilic membrane, as shown by its spontaneous and nearly instantaneous wetting with water.

Example 3

Table 2 below provides data on mechanical properties of unprocessed hydrophobic microporous membranes and the hydrophilic microporous membranes of the present invention, both before and after in-situ conversion to the corresponding PVA shell membrane. The base PE membrane was the same as that used in Example 1. The PVTFA treated membranes were prepared according to the procedure detailed in Example 2, using various concentrations of syndiotactic PVTFA solutions in acetone as noted in Table 2 below. Hydrolysis of the PVTFA treated membranes was performed in an ammonia atmosphere as in Example 1. The PVTFA add-on was determined by weight difference after a piece of the PVTFA treated membrane had been extracted with acetone to a constant weight. The weight percent of PVA was calculated from the weight percent PVTFA above, assuming 100 percent conversion to PVA. Tensile measurements were performed on 2.54 cm wide strips of membrane as described above. Tensile strength is defined as the Newtons/m$^2$ at break normalized to the cross-sectional area.

Example 4

A microporous PE membrane, prepared according to Example 23 of U.S. Pat. No. 4,539,256 (Shipman), having 0.26 micron pore size and a 77 percent porosity was treated with a 4 percent (w/v) solution of syndiotactic PVTFA (prepared according to Example 1) in cyclohexanone. The web was passed through an immersion trough containing the tactic PVTFA solution, which was heated to 46° C. to decrease its viscosity, then passed through a rubber nip station to squeeze off excess solution, and dried in an air floatation oven at a temperature of 40.5° C. to produce a PVTFA treated membrane. Control of the PVTFA add-on was more difficult using this method, and the membrane had a tendency to stretch as it passed through the nip roll station. After hydrolysis with ammonia vapor, as in Example 1, the membrane was hydrophilic as shown by its spontaneous and nearly instantaneous wetting with water.

Example 5

A microporous polypropylene (PP) membrane, made according to the procedure of Example 9 of U.S. Pat. No. 4,726,989 (Mrozinski), the disclosure of which is incorporated herein by reference, was treated with a 4 percent (w/v) acetone solution of syndiotactic PVTFA following the procedure of Example 2. Upon hydrolysis with ammonia vapor as in Example 2, the membrane was hydrophilic, as demonstrated by its spontaneous and nearly instantaneous wetting with water. The porous properties of the starting PP membrane and the hydrophilic membrane of the present invention are shown in Table 3. Pore size loss was less than 11 percent, demonstrating a substantial retention of the physical structure of the membrane while imparting hydrophilicity to the membrane surfaces.

TABLE 2

| | | | Tensile Strength At Break ((Newtons/m$^2$) × 10$^6$) | | Elongation To Break (%) | |
|---|---|---|---|---|---|---|
| Example | Membrane Description Solution Concentration | Weight Percent PVTFA or PVA Add On | MD | TD | MD | TD |
| 3A | Uncoated PE from Ex. 1 | — | 5.76 | 0.32 | 47 | 107 |
| 3B | Ex. "3A" covered with 4% PVTFA | 29.2 | 9.33 | 5.79 | 38 | 53 |
| 3C | Ex. "3B" after conversion to PVA | 9.3 | 10.13 | 6.64 | 66 | 118 |
| 3D | Ex. "3A" covered with 6% PVTFA | 36.1 | 9.82 | 6.40 | 28 | 46 |
| 3E | Ex. "3D" after conversion to PVA | 11.6 | 10.43 | 7.34 | 43 | 97 |
| 3F | Ex. "3A" covered with 8% PVTFA | 42.0 | 9.88 | 6.55 | 20 | 45 |
| 3G | Ex. "3F" after conversion to PVA | 13.4 | 11.62 | 7.97 | 50 | 91 |

TABLE 3

| Sample | Weight Percent PVA Add-On | Thickness | Pore Size | Percent Pore Size Loss | Porosity | Gurley | Water Permeability* |
|---|---|---|---|---|---|---|---|
| PP | — | 0.081 mm | 0.974 μ | — | 82.9% | 3.3 sec | 0** |
| PVA shelled PP | 10.2% | 0.076 mm | 0.874 μ | 11% | 79.2% | 3.7 sec | 0,15 L/(m²*hr*Pascals) |

*Water permeability measured at 68,930 Pascals.
**No flow of water occurs at 68,930 Pascals through this hydrophobic membrane without an ethanol pre-wetting step due to the hydrophobicity of PP. When measured after ethanol pre-wetting and a solvent exchange of water, PP water permeability measured 0.13 L/(m²*hr*Pascals).

Example 6

A 0.023 mm thick PP microporous membrane, prepared according to Example 9 of U.S. Pat. No. 4,726,989, having a 0.2 micron pore size, a 66.7 percent porosity, and a Gurley value of 25.6 sec, was treated with PVTFA according to the procedure of Example 2, using a 2 percent (w/v) solution of syndiotactic PVTFA in acetone followed by in-situ NH$_3$ hydrolysis. The treatment/hydrolysis operation was repeated three times to prepare the hydrophilic membrane of the present invention. The resulting hydrophilic membrane was instantaneously wet with water. The ability of the PVA shell to resist wash-out by water was demonstrated by placing the membrane in boiling water for 5 hours, drying the membrane, and demonstrating that the membrane was still spontaneously and nearly instantaneously wet with water, even though there was a 1.8 percent reduction in the membrane's weight during the exposure to boiling water.

Example 7

The syndiotactic PVTFA treated membrane of Example 1 was placed in a stream of anhydrous NH$_3$ for 2 seconds. The NH$_3$ stream was directed against the membrane so as to force the ammonia through the pores of the membrane. After this dry ammonolysis treatment, the hydrophilicity of the membrane was comparable to the hydrophilicity of the membrane of Example 1, as shown by spontaneous and nearly instantaneous wetting with water. FT-IR showed that 100 percent conversion of the PVTFA to PVA was accomplished. This demonstrated that the 2 minute ammonolysis time of Example 1 was only required in order to allow the NH$_3$ vapor to diffuse into the pores, and that by forcing the NH$_3$ into the pores, the true ease of conversion to PVA is appreciated.

Example 8

The ability to convert syndiotactic PVTFA treated membranes into PVA shell membranes using a variety of hydrolysis reagents and conditions was demonstrated by dipping the PVTFA treated membrane of Example 1 into solutions of various bases as well as a HCl solution. The results are shown in Table 4.

TABLE 4

| Example | Hydrolysis | pH | Immersion Time | Result |
|---|---|---|---|---|
| Comparison 8A | 0.5M HCl in MeOH | <2 | 30 min | not hydrophilic |
| 8B | 0.1M NaOH in MeOH | 13 | 30 min | hydrophilic |
| 8C | 0.1M Na$_2$CO$_3$ IN 50:50.MeOH:H$_2$O | — | 30 min | hydrophilic |
| 8D | 10% conc. NH$_4$OH in MeOH | 8 | 30 min | hydrophilic |
| 8E | 0.1M KOH in H$_2$O | 13 | 30 min | outside surface hydrophilic |
| 8F | 0.1M KOH in H$_2$O | 13 | 4 days | outside surface hydrophilic |

In order to effect the conversion of PVTFA to PVA throughout the membrane, the solution must be able to wet the PVTFA treated membrane, or the base must be volatile in order to deliver the hydrolysis reagent to the internal pore surfaces (c.f Examples 10E and 10F). The 30 minute immersion time was probably excessive, but was chosen to ensure complete hydrolysis. All cases that resulted in a hydrophilic membrane (Examples 10B, 10C and 10D) showed 100 percent conversion of the PVTFA to PVA under FT-IR analysis performed according to Example 1.

Example 9

The PE microporous base membrane of Example 1 was treated, as in Example 2, with 4 percent (w/v) syndiotactic PVTFA solutions in various solvents as noted in the Table 5 below. This example demonstrates that a variety of solvents other than the preferred acetone, including: esters, cyclic ethers, aliphatic and aromatic ketones, nitrites, and amides, can be used to prepare PVTFA treated membranes. Also, shown by comparison, are solvents which could not be made to work, due to the substantial insolubility of PVTFA in these solvents. Copolymers of PVTFA, described in other examples within this disclosure, are not limited to the solvents listed below.

TABLE 5

| Example | Solvent | Coating Conditions | Result |
| --- | --- | --- | --- |
| 9A | Ethyl Acetate | Room Temp. (21° C.) | hydrophilic |
| 9B | Tetrahydrofuran | 40° C. on PE | hydrophilic |
| 9C | Dimethyl Formamide | Room Temp. (21° C.) | hydrophilic |
| 9D | Acetophenone | 80° C. on PP | hydrophilic |
| 9E | Acetonitrile | Room Temp. (21° C.) | hydrophilic |
| Comparison 9F | Diethyl Ether | — | PVTFA not substantially soluble |
| Comparison 9G | 1,1,1-Trichloroethane | — | PVTFA not substantially soluble |
| Comparison 9H | Aliphatic Alcohols (i-PA, EthOH, n-PA, n-BuOH) | | PVTFA not substantially soluble |
| Comparison 9I | Trifluoroacetic Acid | — | PVTFA not substantially soluble |
| Comparison 9J | 1,1,1-Trifluoroethanol | — | PVTFA not substantially soluble |

Example 10

Microporous PE membrane samples, prepared according to Example 23 of U.S. Pat. No. 4,539,256, having a pore size of 0.548μ, a thickness of 0.056 mm, a porosity of 88 percent, and a Gurley value of 5.4 sec, were treated, as in Example 2, with 4 percent (w/v) acetone solution of syndiotactic PVTFA copolymers having either vinyl acetate or maleic anhydride as the comonomer. The copolymers were prepared by free radical polymerization of the appropriate ratio of vinyl trifluoroacetate and the corresponding vinyl comonomer (i.e., vinyl acetate or maleic anhydride, respectively) according to Examples 1 and 4, respectively, of U.S. Pat. No. 4,618,649 (Ofstead), which is incorporated herein by reference. In-situ hydrolysis of these treated membranes produced PVA shell membranes which were hydrophilic as evidenced by spontaneous and nearly instantaneous wetting with water. In order to show that the crystallinity of the hydrophilic PVA shell was not excessively disrupted by the incorporation of less than about 5 percent of comonomer, each PVA shell membrane sample was subjected to a water extraction to determine PVA loss. Initial PVTFA and PVA add-ons were determined according to the procedures of Example 3. One liter of water was passed through a disc of each PVA shell membrane having a surface area of 36.3 cm$^2$ and the resulting PVA weight loss calculated by weight differential of the membrane sample. The weight loss results tabulated in Table 6 show that less than 1 weight percent of the membrane weight was lost due to the water wash step. The hydrophilicity of the washed and dried samples were comparable to the hydrophilicity of the unwashed membranes, demonstrating that the presence of less than about 5% comonomer had not significantly disrupted the crystallinity of the PVA.

TABLE 6

| Example | Copolymer | % Weight Add-On | Loss* |
| --- | --- | --- | --- |
| 10A | PVTFA-co-MA (99.7/0.3) | 12.2 | −0.25 |
| 10B | PVTFA-co-MA (99.9/0.1) | 8.5 | −0.05 |
| 10C | PVTFA-co-MA (99.95/0.05) | 10.1 | −0.10 |
| 10D | PVTFA-co-VA (96.0/4.0) | 9.5 | 0.85 |
| 10E | PVTFA-co-VA (98.5/1.5) | 9.2 | 0.30 |

*Negative weight loss indicates a net weight gain. Even though care was taken to use pre-filtered water for the flushing, some particulate matter may have collected on the membrane, or these numbers may simply reflect the inherent imprecision of the weight measurement. In any case there was a negligible weight loss due to flushing these samples with water.

Example 11

A microporous polysulfone membrane having a surfactant coating to render it hydrophilic and having a rated 0.45 micron pore size (obtained from Schleicher & Schuell) was rinsed in isopropyl alcohol to remove the surfactant coating. The then hydrophobic polysulfone membrane was saturation-treated with a 4 percent (w/v) solution of syndiotactic PVTFA in acetophenone (a poor solvent for polysulfone) following the procedure of Example 2. The resulting PVTFA treated membrane was hydrolyzed in an ammonia atmosphere according to the procedure of Example 2 to produce a hydrophilic PVA shell membrane which was spontaneously and nearly instantaneously wet with water.

Example 12

A microporous polyvinylidene fluoride, PVDF, membrane made according to Example 22 of U.S. Pat. No. 4,539,256, having a 0.21 micron pore size, a 72 sec Gurley value and a 58.3 percent porosity, was saturation-treated with a 4 percent (w/v) solution of syndiotactic PVTFA by forcing the solution through the membrane by applying a partial vacuum to the opposite side of the membrane. The resulting PVTFA treated membrane was hydrolyzed in an ammonia atmosphere according to the procedure of Example 2 to produce a hydrophilic membrane that was spontaneously and nearly instantaneously wet with water.

Example 13

Polyethylene microporous membranes, prepared according to Example 23 of U.S. Pat. No. 4,539,256, having a range of porosities and pore sizes, were treated with a 4 percent (w/v) solution of syndiotactic PVTFA in acetone according to the procedure of Example 1. Upon hydrolysis with the ammonia vapor according to the procedure of Example 2, hydrophilic PVA shell membranes which were spontaneously and nearly instantaneously wet with water were produced. The porosity, pore size and Gurley values of both the starting membranes, numbers 13A, 13C, 13E, and 13G, and the PVA shell membranes, numbers 13B, 13D, 13F, and 13H, are tabulated in Table 7, along with comments concerning the amount of surface pore blockage that occurred. The extensive pore blockage noted with the 0.101 μm pore size membrane is due to the fact that the solution evaporates more rapidly than it can penetrate into the small pores which results in the formation of a pore-blocking skin at the surface of the membrane. Solvents having lower vapor pressures and/or lower viscosity solutions should lessen the occurrence of this type of pore-blocking skin formation.

TABLE 7

| Sample # | Porosity (%) | Pore Size (μm) | Pore Size Loss (%) | Gurley (secs) | Comments |
|---|---|---|---|---|---|
| 13A | 82.2% | 0.479 | — | 9.9 | |
| 13B | 76.3% | 0.427 | 12% | 12.6 | No pore blockage |
| 13C | 78.5% | 0.213 | — | 29.0 | |
| 13D | 74.5% | 0.098 | 54% | 121.0 | Some pore blockage |
| 13E | 76.3% | 0.149 | — | 53.4 | |
| 13F | 68.9% | 0.102 | 33% | 184.3 | Some pore blockage |
| 13G | 57.8% | 0.101 | — | 269.7 | |
| 13H | 47.5% | <<0.1 | ~100% | >>1K | Complete surface pore blockage |

Example 14

The procedure of Example 1 was used to prepare a hydrophilic PVA shell membrane from a microporous PE membrane having a pore size of 0.259 microns and a 77 percent porosity, prepared according to Example 23 of U.S. Pat. No. 4,539,256, except that a 4.7 percent (w/v)solution of syndiotactic PVTFA in cyclohexanone was used, and the two zones of the oven were set to 38° C. and 106° C. respectively. The higher viscosity of the cyclohexanone PVTFA solutions relative to the viscosity of the acetone PVTFA solutions coupled with the relatively high oven temperatures used to dry the treated membranes resulted in the formation of an integral pore-blocking skin on the membrane surface. The presence of the skin was demonstrated by an effectively infinite Gurley air permeability value and by SEM analysis.

Example 15

Samples of hydrophilic microporous membranes were prepared according to Example 1 and were subjected to extractions by highly polar organic solvents to demonstrate the ability of the PVA shell to resist wash-out. The initial PVA add-on was 9.1 weight percent of the untreated hydrophobic microporous membrane. The samples were weighed and then soaked for 1.5 hours in the indicated solvents, followed by four rinses of water to remove the solvent. The samples were dried, reweighed and a percentage weight loss for the hydrophilic membrane calculated by weight differential.

Samples exposed to each of the above solvents remained hydrophilic to varying degrees. Dimethyl formamide (DMF) caused the greatest percentage weight loss of the PVA shell, perhaps because the DMF dissolves the PVA crystallites (c.f FIG. 3). Thus, while the hydrophilic polymeric structure produced according to the present invention is resistant to washout by DMF at least after continuous exposure for up to 1.5 hours, care should be taken to select a polymeric structure which does not also degrade or dissolve during exposure to the highly polar solvent.

TABLE 8

| Example | Solvent | Sample Percent Weight Loss | Polyvinyl Alcohol Shell Percent Weight Loss |
|---|---|---|---|
| 15A | Dimethylsulfoxide [DMSO] | 0.7 | 8.0 |
| 15B | Dimethylformamide [DMF] | 3.7 | 40.5 |
| 15C | Glycerol | 0.5 | 5.5 |
| 15D | Ethylene Glycol [EtGLY] [GLY] | 0.2 | 2.2 |

Example 16

An inherently hydrophilic microporous Nylon 6,6 membrane, rated with a 0.45 micron pore size, obtained from Schleicher & Schuell of Keene, N.H., was saturation-covered with a 4 percent w/v acetone solution of syndiotactic PVTFA following the procedure of Example 2. The resulting PVTFA envelopment of the internal and external surfaces of the membrane did not block the pores, but due to the hydrophobicity of PVTFA, the Nylon 6,6 membrane was rendered hydrophobic. Upon reaction with the ammonia vapor of ammonium hydroxide, as in Example 2, the PVA shell membrane again became hydrophilic as demonstrated by spontaneous and nearly instantaneous wetting with water. Characterization data, before and after this treatment are tabulated in Table 9, below. This example demonstrated the use of the present treatment to provide hydroxyl functional groups to the surface of a hydrophilic membrane without significantly blocking the pores or reducing the hydrophilicity.

TABLE 9

| Example | Condition | Pore Size | Pore Size Loss | Gurley | Porosity |
|---|---|---|---|---|---|
| 16A | Uncovered | 0.771 μ | — | 14 sec | 61.7% |
| 16B | PVA Shell | 0.740 μ | 5% | 24 sec | 60.4% |

Example 17

A piece of Gore-Tex™ poly(tetrafluoroethylene) membrane, manufactured by W. L. Gore and Associates, Inc. of Elkton, Md. was saturated with a 5 percent w/v acetone solution of syndiotactic PVTFA prepared according to Example 1 using a #14 wire-wound bar to spread the solution. This sample was allowed to dry at room temperature in a ventilation hood to produce a PVTFA shell on the external and internal surfaces of the membrane, without causing pore blockage or PVTFA skin formation, as shown by SEM examination. The sample was reacted with vaporous ammonia as in Example 1 to yield a highly hydrophilic membrane, as shown by being spontaneously and nearly instantaneously wetted with water.

Example 18

A piece of a calendered spunbonded PE web, commercially available under the trademark "Tyvek T-984", from E. I. DuPont of Wilmington, Del., having an average Gurley air flow of 3.1 sec per 50 cm³ of air, was saturation-covered with a 4 percent w/v acetone solution of syndiotactic PVTFA according to the procedure of Example 2. After drying and reacting in-situ with ammonia vapor, the PVA shell web was hydrophilic as judged by being spontaneous and nearly instant wettability with water. The web was still through-porous, since water would pass through the web after the hydrophilization and exhibited a Gurley value of 9.8 sec per 50 cc of air.

Example 19

A polypropylene melt-blown web, was made according to the procedure described in Wente, Van A., "Superfine Thermoplastic Fibers" in Engineering Chemistry, Vol. 48, p. 1342 et. seq. (1956), or in Report No. 4364 of the Naval Research Laboratories, published May 25, 1954, entitled "Manufacture of Superfine Organic Fibers", by Wente, V. A.; Boone, C. D.; and Fluharty, E. L., the disclosures of which are incorporated by reference herein. It was covered with a 6 percent w/v acetone solution of syndiotactic PVTFA according to the procedure of Example 2. After drying and in-situ reaction with ammonia vapor, this PVA shell melt-blown web was hydrophilic as demonstrated by spontaneous and nearly instant wetting with water. The resistance of this hydrophilic treatment to washout was demonstrated by 16 repeated soak/squeeze/dry cycles with pure water, resulting in a melt-blown web that was still as hydrophilic as it was initially, as shown by spontaneous and nearly instant wettability with water.

Example 20

A polypropylene woven fabric, obtained from the Arthur Kahn Co., of N.Y., N.Y., which was hydrophobic (i.e., a drop of water did not penetrate the fabric when it was placed on the fabric gently) was covered with a 4 percent w/v solution of syndiotactic PVTFA in acetone using the method of Example 2. (The weave of the starting fabric was coarse enough, however, to allow water to penetrate if any pressure was applied to the drop.) This resulted in a shell of PVTFA enveloping the surface of the fabric's fibers. Upon reaction of the PVTFA covered fabric with the ammonia vapor of ammonium hydroxide, as in Example 2, the fabric having a PVA shell about its surfaces became hydrophilic as demonstrated by spontaneous and nearly instant wetting with water.

Example 21

In order to show the availability of the hydroxyl functional groups of the hydrophilic shell towards chemical derivatization, the hydrophilic membrane from Example 1 was reacted with an acid chloride. Enough sebacyl chloride was added to a glass vessel to cover a piece of the vacuum dried membrane placed in the vessel. These were allowed to react for ½ hour at room temperature. The sample was rinsed in 1,1,1-trichloroethane to remove excess acid chloride. Infrared spectroscopy of the reacted membrane showed a new carbonyl absorption at $1737^{-1}$ cm and a decrease in the hydroxyl absorption at $3300^{-1}$ cm, which indicated that esterification of the hydroxyl group had occurred.

Example 22

A microporous polypropylene (PP) membrane, made by thermally induced phase separation as disclosed in U.S. Pat. No. 4,726,989 (Mrozinski), Example 9, having a Bubble Point maximum pore size of 0.65 µm, an average Gurley of 6.4 sec per 50 cc of air and a thickness of 0.82 mm was extrusion saturated with a 4.5 percent (w/v) solution of syndiotactic PVTFA according to procedure of Example 1 except that the membrane was dried for about 45 seconds. The resulting treated membrane had a PVTFA add-on of 25.6 percent. A PVA shell membrane was prepared by hydrolyzing the PVTFA treated membrane in a stream of anhydrous ammonia according to the procedure of Example 9, followed by hydration with deionized water and drying at room temperature for about four (4) minutes. The PVA shell membrane had a Bubble Point pore size of 0.575 µm and was hydrophilic as demonstrated by it being spontaneously and nearly instantly wetted with water.

The filtration performance of the PVA shell membrane, the untreated PP microporous membrane and a commercially available microporous membrane, namely a 0.22 µm Durapore™ polyvinylidene difluoride microporous membrane (available from Millipore Corp, Bedford, Mass.) were compared by measuring the turbidity of the filtrate obtained when each membrane was challenged with a submicron sized suspension. A Hach Ratio Turbidimeter (Model 18900), available from Hach Instruments (Fort Collins, Col.) was used to determine filtrate turbidity. The challenge suspension was prepared by adding six drops of a Fastek 0.22 µm sized latex sphere suspension (formerly available from Eastman Kodak) to 1600 ml of ultrapure water which had a turbidity of 0.08 Nephelometric Turbidity Units (NTU) to produce a suspension having a turbidity of 117 NTU. A 47 mm diameter disk of the test membrane was placed on the support plate of a Gelman Magnet Filter Holder, the top of the filter holder installed and the filter holder placed on a vacuum filtration flask. A laboratory vacuum of approximately 56 cm Hg was applied to the filter flask and the average time required to collect 100 ml of filtrate for each membrane filter and the turbidity of each filtrate sample as measured on the Hach Turbidimeter are reported in Table 10.

TABLE 10

| Membrane Sample | Time/100 ml Filtrate (seconds) | Turbidity (NTU) |
| --- | --- | --- |
| PP Membrane | 90* | 1.62 |
| PVA Shell Membrane | 195 | 0.325 |
| Durapore Membrane | 155 | 5.4 |

*There was no flow through the untreated membrane until it had been wet with isopropanol.

The data in Table 10 shows that the microporous membrane filter based on the PVA shell membrane of the present invention has significantly better particle retention properties than the untreated membrane as is evidenced by the lower turbidity of the filtrate obtained using the PVA shell membrane. Reasonably close filtration rates between the PVA shell membrane and the Durapore membrane implies that the two membranes have porosities which are quite similar but the lower turbidity of the filtrate obtained with the PVA shell membrane suggests that it is likely that the PVA shell membrane has either a smaller pore size or a higher tortuosity as compared to the Durapore membrane and consequently it can provide superior filtration performance.

Microporous membrane filters known to provide absolute control over bacterial contaminants above a critical size can be used to "cold pasteurize" or sterilize thermally sensitive aqueous fluids. Several techniques are used to validate the retentive efficiency, compatibility, and life expectancy of filters with an absolute pore-size rating above 0.02 µm. While a rigorous validation of filter efficiency requires the use of several techniques, an indication of filter efficiency can be provided by challenging the filter with 0.22 µm latex particle and comparing the concentration of spheres up- and downstream of the filter by means of turbidimetric analysis (see Goldsmith et. al., Pharmaceutical Manufacturing, November 1985, pp 31–37). The data in Table 10 suggests that the PVA shell membranes of the present invention have the potential of realizing an "absolute" rating for control of particles larger than 0.22 μm and thus, might be suitable for sterilization of aqueous fluids.

Example 23

A 0.05 mm thick hydrophobic microporous polyethylene membrane having 70 percent void volume prepared according to Example 23 of U.S. Pat. No. 4,539,256 and a second like membrane prepared according to the procedure of Example 1, were used as substrates. The unmodified polyethylene membranes were presoaked in acetone and then in pH 6.3 aqueous citrate buffer solution prior to coating to improve wetting characteristics. The hydrophilic microporous polyethylene membrane was used as received. The enzyme used was a special-grade, high-purity glucose oxidase powder (having a "Finnsugar stated activity" of 110 units/mg) from Finnsugar Biochemicals, Inc. of Schaumberg, Ill. Enzyme solutions were prepared using this powder and 0.1M, pH 6.3 citrate buffer of food-grade quality prepared using 27.9 g citric acid trisodium salt dihydrate, 0.98 g citric acid, and 1 liter of deionized water. Reagents for buffer preparation were obtained from Sigma Chemical Company of St. Louis, Mo.

Twelve membrane disks of 15.5 cm² apparent exterior surface area were saturated with 55 microliters of a 0.65 mg/ml glucose oxidase enzyme solution prepared in pH 6.3 citrate buffer. Thus, each disk was coated with approximately 0.04 mg of enzyme. The saturated disks were dried in a desiccator at room temperature and pressure for several hours prior to testing.

The enzyme solution did not wet out well on the disks prepared using the pre-wetted, hydrophobic, microporous polyethylene membrane.

Oxygen utilization rates were determined using a Model 5300 Biological Oxygen Monitor equipped with Model 5331 Standard Oxygen Probes and a constant temperature bath operating at 30° C. (Yellow Springs Instrument (YSI) Company, Inc., Scientific Division). The oxygen probes measure oxygen utilization in well-mixed, air saturated test solutions. For each test, 1000 microliters of a 30% w/v glucose solution were used as the substrate and an additional 2000 microliters of citrate buffer were included. The microporous membrane was tested in the air-saturated solution; small disks (20 mm²) of membrane were attached to the stirrer in the oxygen monitor test vial. Since each test solution and membrane were well-mixed and in intimate contact, the oxygen utilization rate was assumed to be uniform throughout the test vial.

Four types of samples were tested using the YSI Biological Oxygen Monitor: blank solution; enzyme stock solution; enzyme-loaded, pre-wetted, hydrophobic, microporous polyethylene membrane, and enzyme-loaded, hydrophilic, microporous polyethylene membrane. Table 16 lists oxygen utilization rates for the samples. As anticipated, the blank solution did not exhibit any oxygen uptake and the enzyme stock solution exhibited a very high oxygen uptake. The enzyme-loaded hydrophobic microporous polyethylene membrane sample exhibited a lower oxygen uptake than the microporous polyethylene membrane.

TABLE 11

Oxygen Utilization Rates For Various Glucose Oxidase Enzyme-Loaded Microporous Polyethylene Membranes

| Sample Description | Oxygen Uptake (μl $O_2$/mg enzyme-hr) |
|---|---|
| Blank Solution | 0 |
| Stock Solution (0.65 mg/ml glucose oxidase) | 112,000 |
| Hydrophobic, Microporous Polyethylene Membrane (pre-wetted prior to coating) | 15,400 |
| Hydrophilic, Microporous Polyethylene Membrane: | |
| Sample 1 | 53,100 |
| Sample 2 | 35,700 |
| Sample 3 | 39,300 |
| Sample 4 | 35,800 |
| Sample 5 | 39,100 |
| Sample 6 | 54,700 |

Example 24

In order to demonstrate that the glucose oxidase-loaded, hydrophilic polyethylene membrane is effective in removing oxygen from the headspace of a container, the following product test was performed.

For each of twenty four samples, a 25 mm diameter glass vial having a polyethylene snap-cap and a height of 25 mm was filled using 12 ml of deionized water. This provided a headspace of approximately 4.5 cm³ in the vial. The oxygen volume in this headspace was approximately 1 cm³.

The inside surface of each snap-cap was coated with 0.1 ml of a gelatin solution of the following composition: 6.7 g "Knox™" gelatin (available from Knox Gelatine Inc., Englewood Cliffs, N.J.), 154 g dextrose (available from Fisher Scientific, Inc.), and 225 ml deionized water. This quantity of solution provided a glucose concentration of 0.068 g of glucose.

To supply the enzyme for the reaction, 25 mm diameter disks of hydrophilic microporous polyethylene membrane prepared according to Example 1 were loaded with 50 μl of a solution containing 2.5 mg/ml glucose oxidase enzyme, 10 weight percent sucrose (available from Sigma Chemical Company), and pH 6.3 citrate buffer. This provided 0.125 mg glucose oxidase for the reaction. The loaded disks were placed on a polytetrafluoroethylene (PTFE) sheet and dried in a circulating air oven for 10 minutes at 45° C. The disks were then removed from the PTFE sheet and placed onto the gelatin-coated vial caps to which approximately 50 μl of pH 6.3 citrate buffer/10 weight percent sucrose solution had been added. All vials were sealed using the coated snap-caps prepared as described above.

Vials were stored in a refrigerator at 5° C. Vials were tested periodically to determine headspace oxygen content. These tests were performed using a MOCON/Toray LC700F Oxygen Headspace Analyzer available from Modern Controls, Inc., of Minneapolis, Minn. Oxygen content was found to decrease exponentially over a period of 1000 hours according to the equation y=19.7*e (−0.01x), where y is the oxygen content in the package headspace in percent and x is the time since sample preparation in hours.

Example 25

An experiment was performed to directly coat glucose and glucose oxidase enzyme solutions together onto hydrophilic microporous polyethylene membrane prepared according to the procedure of Example 1. The glucose solution was prepared using 500 g of dextrose, 1000 ml of pH 6.3 citrate buffer, and 2 g of granular potassium sorbate as a mold inhibitor (available from Monsanto Company, St. Louis, Mo.). The enzyme solution was prepared using 180 ml of pH 6.3 citrate buffer with an enzyme concentration of 2.5 mg/ml.

Each solution was placed in a separate three-necked, round-bottom flask with a base stopcock. The solutions were degassed using an aspirator and then back-flushed using nitrogen. The enzyme solution was fed into the flask containing the glucose solution. The two solutions were mixed.

Several milliliters of the mixed solution were coated onto hydrophilic microporous membrane using a glass bar. The membrane samples were dried in a forced-air oven for ten minutes at 90° F. The samples were then immediately placed in a polyethylene bag containing $CaSO_4$ desiccant available from W. A. Hammond Drierite Company, Xenia, Ohio.

Samples of 100 mm$^2$ dimension were cut from the coated membranes. These membranes were tested to determine activity using a YSI Biological Oxygen Monitor. The samples were tested in three milliliters of pH 6.3 citrate buffer at 30° C. approximately 72 hours after preparation. These membranes exhibited an average oxygen uptake of 0.175 cm$^3$/hr under the above test conditions.

Example 26

Glucose oxidase enzyme from Finnsugar Biochemicals, Inc. having a "Finnsugar stated activity" of 110 units/mg was added in a concentration of 2.5 mg/ml into a pH 6.3 citrate buffer aqueous solution containing 10% (w/v) sucrose. Hydrophilic membrane prepared according to Example 1 was saturated using rotogravure coating equipment. A 120P gravure roll was used on the coating equipment to load the enzyme system onto the hydrophilic microporous membrane's complex geometric configuration. The membrane was saturated with enzyme system because the citrate buffer aqueous solution wet the hydrophilic shell enveloping the porous membrane. The coating equipment was operated at a line speed of 4.6 m/min. and at a drying set-point temperature of 65° C. The dried, enzyme-loaded membranes were stored in a polyethylene bag containing $CaSO_4$ desiccant for two months prior to use, in order to simulate production storage times.

Independently, a nonwoven web of Nylon 6 commercially available from Allied Chemical under the brand "CFX Nylon 6" and having a basis weight of 53 g/m$^2$ was oriented and embossed at 175° C. This nonwoven web was coated with a 50% aqueous solution of glucose also containing 0.2 weight percent of potassium sorbate for preservative purposes. The coating die was a fluid-bearing die. The coating occurred at a line speed of 1.5 m/min. A drying temperature of 111° C. was used. A coating weight of 2.3 g of glucose/ 150 cm$^2$ was obtained.

The enzyme-loaded membrane and the glucose coated web were used in combination to form an absorbent pad for lunchmeat packaging. The meat packaged was 2.5 oz. "Carl Buddig Chicken" a smoked meat product commercially available from Carl Buddig and Company of Chicago, Ill. Both the enzyme-loaded membrane and the glucose coated web were cut into 10 cm×12.5 cm pieces. The loaded membrane was placed on top of the coated web, with the enzyme-loaded membrane contacting the smoked chicken.

This combination was packaged in "Kapak" KSP410-1 Mb barrier pouches commercially available from Kapak Corporation of Minneapolis, Minn. and cut to dimensions of 15 cm×20 cm. The pouches had a 0.6 cm heat seal on three edges. The fourth edge was heat sealed using a "Sentinel™" brand, bar-type heat-sealer commercially available from Packaging Industries Group, Inc. of Hyannis, Mass. The sealing conditions were 150° C. at a pressure of $4.1\times10^5$ Pa and one second exposure time.

The sealed lunchmeat pouches were then stored at 5° C., and oxygen content was monitored periodically over the next five days. Oxygen content was determined using an "LC-700F MOCON/Toray" oxygen headspace analyzer. Oxygen content was found to decrease exponentially over the five day period according to the equation: $y=17.1*e^{(-0.64x)}$, where y is the oxygen content in the package headspace in percent and x is the time since sample preparation in days. The headspace oxygen content decreased from about 21% upon heat sealing to approximately 3.5% on the third day to approximately 0.7% on the fifth day. By comparison, a smoked chicken package with the membrane prepared according to Example 1 above but without the enzyme-loaded therein retained about a 17% headspace oxygen content on the third day.

Neither the embodiments of the invention nor the examples described above limit the scope of this invention.

What is claimed is:

1. An oxygen scavenger to protect oxygen sensitive products, comprising: a hydrophilic porous supporting structure having a complex geometric configuration of hydrophilic surfaces and an enzyme system loaded on said hydrophilic surfaces to catalyze at said hydrophilic surfaces a reaction to consume the oxygen, wherein said hydrophilic porous supporting structure further comprises a membrane having pores of from about 0.01 μm to about 20 μm, and wherein said hydrophilic porous supporting structure further comprises a tactic, hydrophilic poly(vinyl alcohol) shell enveloping said surfaces while substantially retaining said complex geometric configuration.

2. The oxygen scavenger according to claim 1, wherein said enzyme system is loaded onto said surfaces in a water-miscible solvent system which wets said surfaces.

3. The oxygen scavenger according to claim 2, wherein said shell is between about an average of 10 monolayers to about an average of 4000 monolayers thick on said surfaces and said enzyme system is a layer in a minimally useful amount without blocking pores.

4. The oxygen scavenger according to claim 2, wherein said shell is substantially insoluble in water or organic solvents and the water and the oxygen in the reaction may penetrate said porous structure.

5. The oxygen scavenger according to claim 1, wherein pores of said structure permit the flow of oxygen and $H_2O$ to said enzyme system loaded on said surfaces, in order to catalyze the reaction which consumes oxygen at said surfaces remote from the oxygen sensitive product.

6. The oxygen scavenger according to claim 1, wherein said enzyme system is selected from a group consisting of glucose oxidase; a glucose/glucose oxidase combination; a glucose oxidase/sucrose combination; a starch/amylase/ glucose oxidase combination; a cellulose/cellulase/glucose oxidase combination; a milk powder/lactase/glucose oxidase combination; a glucose oxidase/fructose isomerase/fructose combination; a glucose oxidase/lactase/whey solids/lactose combination; a glucose/lactase/lactose combination; a glucose oxidase/maltase/starch combination; a glucose oxidase/ maltase/maltose combination; a mushroom tyrosinase/ tyrosine combination; a glucose oxidase/sucrose/sucrase combination; any combination of Edben-Meyerhoff-Citric Acid cycle enzymes; and combinations thereof.

7. An oxygen scavenging package to protect an oxygen sensitive product, comprising:

(a) a barrier package capable of being sealed to minimize intrusion or molecular oxygen into the package, and (b) an oxygen scavenger according to claim 1;

wherein pores of said structure permit the flow of oxygen and H₂O to said enzyme system loaded on said surfaces, in order to catalyze the reaction which consumes oxygen at said surfaces remote from the oxygen sensitive product.

8. The oxygen scavenging package according to claim 7 wherein said enzyme system is selected from the group consisting of of glucose oxidase; a glucose/glucose oxidase combination; a glucose oxidase/sucrose combination; a starch/amylase/glucose oxidase combination; a cellulose/cellulase/glucose oxidase combination; a milk powder/lactase/glucose oxidase combination; a glucose oxidase/fructose isomerase/fructose combination; a glucose oxidase/lactase/whey solids/lactose combination; a glucose/lactase/lactose combination; a glucose solids/lactose combination; a glucose/lactase/lactose combination; a glucose oxidase/maltase/starch combination; a glucose oxidase/maltase/maltose combination; a glucose oxidase/sucrose/sucrase combination; any combination of Ebden-Meyerhoff-Citric Acid cycle enzymes; and combinations thereof.

9. The oxygen scavenging package according to claim 7, wherein pores of said structure permit the flow of oxygen and H₂O to said enzyme system loaded on said surfaces, in order to catalyze the reaction which consumes oxygen at said surfaces remote from the oxygen sensitive product.

10. The oxygen scavenging package according to claim 7, wherein said supporting structure is a polyolefin membrane rendered hydrophilic and having pores of from about 0.01 μm to about 20 μm.

11. The oxygen scavenging package according to claim 10, wherein said hydrophilic porous supporting structure further comprises a tactic, hydrophilic poly(vinyl alcohol) shell enveloping said surfaces while substantially retaining said complex geometric configuration.

12. The oxygen scavenging package according to claim 10, wherein said enzyme system is loaded on said surfaces in a water-miscible solvent system which wets said surfaces.

13. The oxygen scavenging package according to claim 10, wherein said shell is between about an average of 10 monolayers to about an average of 4000 monolayers thick on said surfaces and said enzyme system is a layer in a minimally useful amount without blocking pores.

14. The oxygen scavenging package according to claim 10, wherein said shell is substantially insoluble in water or organic solvents and the water and the oxygen in the reaction may penetrate said porous structure.

* * * * *